(12) United States Patent
Mazutis et al.

(10) Patent No.: US 11,326,196 B2
(45) Date of Patent: May 10, 2022

(54) SYSTEM AND METHOD FOR SYNTHESIS OF DNA PARTICLES AND USE THEREOF

(71) Applicants: VILNIUS UNIVERSITY, Vilnius (LT); ETH ZURICH, Zürich (CH)

(72) Inventors: Linas Mazutis, Vilnius (LT); Greta Stonyte, Vilnius (LT); Vaidotas Kiseliovas, Vilnius (LT); Rapolas Zilionis, Vilnius (LT); Arvydas Janulaitis, Vilnius (LT); Robertas Galinis, Zürich (CH); Sabine Studer, Zürich (CH); Donald Hilvert, Zürich (CH)

(73) Assignees: VILNIUS UNIVERSITY, Vilnius (LT); ETH 7LIRICH, Zürich (CH)

( * ) Notice: Subject to any disclaimer, the term of this patent is extended or adjusted under 35 U.S.C. 154(b) by 455 days.

(21) Appl. No.: 16/069,404

(22) PCT Filed: Jan. 10, 2017

(86) PCT No.: PCT/IB2017/050124
§ 371 (c)(1),
(2) Date: Jul. 11, 2018

(87) PCT Pub. No.: WO2017/122128
PCT Pub. Date: Jul. 20, 2017

(65) Prior Publication Data
US 2019/0002943 A1 Jan. 3, 2019

Related U.S. Application Data

(60) Provisional application No. 62/276,995, filed on Jan. 11, 2016.

(51) Int. Cl.
*C12P 19/34* (2006.01)
*B01J 19/00* (2006.01)
*A61K 9/50* (2006.01)
*B01L 3/00* (2006.01)

(52) U.S. Cl.
CPC ............... *C12P 19/34* (2013.01); *A61K 9/50* (2013.01); *B01J 19/0093* (2013.01); *B01L 3/502784* (2013.01); *B01J 2219/0086* (2013.01); *B01J 2219/00912* (2013.01); *B01L 2200/027* (2013.01); *B01L 2200/0636* (2013.01)

(58) Field of Classification Search
CPC .............................. C12P 19/34; B01L 3/5027
See application file for complete search history.

(56) References Cited

U.S. PATENT DOCUMENTS 9,737,557 B2   8/2017   Hammond et al.

FOREIGN PATENT DOCUMENTS

WO   2014/134029 A1   9/2014
WO   2015/088299 A1   6/2015

OTHER PUBLICATIONS

Danilevich, Microparticles from Condensed DNA Formed in the Process of Polymerase Chain Reaction, Russian Journal of Bioorganic Chemistry, 35(2):207-218, 2009. (Year: 2009).*
Kottur, Pyrophosphate hydrolysis is an intrinsic and critical step of the DNA synthesis reaction, Nucleic Acids Research, 46(12):5875-5885, 2018. (Year: 2018).*
Xu, Real-time Detection of Loop-Mediated Isothermal Amplification Reaction on Microfluidic Chip, 2011 5th International Conference of Bioinformatics and Biomedical Engineering, DOI 10.1109/icbbe.2011.5780331, pp. 1-3, 2011. (Year: 2011).*
Mazutis, Droplet-based microfluidic systems for high-throughput single DAN molecule isothermal amplification and analysis, Anal. Chem., 81(12): 4813-4821, 2009; Supporting Information. (Year: 2009).*
Heyries, K.A., et al., Megapixel digital PCR. Nature Methods. 2011. 8(8): p. 649-U64.
Devonshire, A.S., et al., Highly Reproducible Absolute Quantification of Mycobacterium tuberculosis Complex by Digital PCR. Anal Chem, 2015. 87(7): p. 3706-3713.
Pekin, D., et al., Quantitative and sensitive detection of rare mutations using droplet-based microfluidics. Lab on a Chip, 2011. 11(13): p. 2156-2166.
Bizouarn, F., Introduction to Digital PCR. Quantitative Real-Time Pcr: Methods and Protocols, 2014. 1160: p. 27-41.
Zhao, Y., et al., Isothermal Amplification of Nucleic Acids. Chem Rev, 2015. 115(22): p. 12491-545.
Mazutis, L., et al., Droplet-based microfluidic systems for high-throughput single DNA molecule isothermal amplification and analysis. Anal Chem, 2009 81(12): p. 4813-21.
Park, N., et al., A cell-free protein-producing gel. Nat Mater, 2009. 8(5): p. 432-7.
Oetting, F.L. and R.A. McDonald, The Thermodynamic Properties of Magnesium Orthophosphate and Magnesium Pyrophosphate. The Journal of Physical Chemistry, 1963. 67(12): p. 2737-2743.
Shopsowitz, K.E., et al., RNAi-microsponges form through self-assembly of the organic and inorganic products of transcription. Small, 2014. 10(8): p. 1623-33.

(Continued)

*Primary Examiner* — Samuel C Woolwine
*Assistant Examiner* — Carolyn L Greene
(74) *Attorney, Agent, or Firm* — Nixon & Vanderhye

(57) ABSTRACT

Disclosed is a system and method for production of DNA particles and use thereof. The DNA particles can be produced by amplification of nucleic acid molecule(s). Alternatively, DNA particles can be prepared by condensing multiple DNA molecules. The DNA condensation into a particle is mainly triggered by pyrophosphate and positively charged cations (e.g. magnesium). DNA particles can be applied for numerous biological applications but not limited to directed evolution, proteomics, drug delivery and imaging. DNA particles can be used to synthesize proteins using in vitro transcription/translation reaction.

10 Claims, 13 Drawing Sheets

Specification includes a Sequence Listing.

(56) References Cited

OTHER PUBLICATIONS

Bloomfield, V.A., DNA condensation by multivalent cations. Biopolymers, 1997. 44(3): p. 269-282.
Mazutis, L., et al., Single-cell analysis and sorting using droplet-based microfluidics. Nat Protoc, 2013. 8(5): p. 870-91.
Danilevich, V.N., et al., The structural peculiarities of condensed DNA micro- and nanoparticles formed in PCR. Journal of Biomolecular Structure & Dynamics, 2014. 32(12): p. 1979-1992.
Danilevich, V.N., et al., New insight into formation of DNA-containing microparticles during PCR: the scaffolding role of magnesium pyrophosphate crystals. Journal of Biomolecular Structure and Dynamics, 2015: p. 1-15.
Zhu, G.Z., et al., Noncanonical Self-Assembly of Multifunctional DNA Nanoflowers for Biomedical Applications. Journal of the American Chemical Society, 2013. 135(44): p. 16438-16445.
Hu, R., et al., DNA Nanoflowers for Multiplexed Cellular Imaging and Traceable Targeted Drug Delivery. Angewandte Chemie-International Edition, 2014. 53(23): p. 5821-5826.
Lee, J.B., et al., Self-assembled RNA interference microsponges for efficient siRNA delivery. Nature Materials, 2012. 11(4): p. 316-322.
Mazutis, L., et al., Multi-step microfluidic droplet processing: kinetic analysis of an in vitro translated enzyme. Lab on a Chip, 2009. 9(20): p. 2902-8.
Lee, S.Y., et al., Biophysical and chemical handles to control the size of DNA nanoparticles produced by rolling circle amplification. Biomaterials Science, 2016. 4(9): p. 1314-1317.
Kahn, J.S., et al., DNA Microgels as a Platform for Cell-Free Protein Expression and Display. Biomacromolecules, 2016. 17(6): p. 2019-2026.
Wolf, S.G., et al., DNA protection by stress-induced biocrystallization. Nature, 1999. 400(6783): p. 83-85.
Galinis, R., et al., DNA Nanoparticles for Improved Protein Synthesis In Vitro. Angew Chem Int Ed Engl, 2016. 55(9): p. 3120-3.
Mazutis et al., Droplet-Based Microfluidic Systems for High-Throughput Single DNA Molecule Isothermal Amplification and Analysis, Anal. Chem. 2009, 81, 4813-4821.
Ottesen et al., "Microfluidic digital PCR enables multigene analysis of individual environmental bacteria", Science, 2006, pp. 1464-1467, vol. 314, No. 5804.
Beer et al., "On-chip, real-time, single-copy polymerase chain reaction in picoliter droplets". Analytical Chemistry, 2007, pp. 8471-8475, vol. 79, No. 22.
Vogelstein et al., "Digital PCR", Proceedings of the National Academy of Sciences of the United States of America, 1999, pp. 9236-9241, vol. 96, No. 16.
Day et al., "Digital PCR strategies in the development and analysis of molecular biomarkers for personalized medicine", Methods, 2013, vol. 59, No. 1.
Dean et al., "Rapid amplification of plasmid and phage DNA using Phi 29 DNA polymerase and multiply-primed rolling circle amplification" Genome Research, 2001, pp. 1095-1099, vol. 11, No. 6.
Shimizu et al., "Cell-free translation reconstituted with purified components", Nature Biotechnology, 2001, pp. 751-755, vol. 19, No. 8.
Asahara et al., "In vitro genetic reconstruction of bacterial transcription initiation by coupled synthesis and detection of RNA polymerase holoenzyme", Nucleic Acids Research, 2010, e141, vol. 38, No. 13.
Lesley et al., "Use of in vitro protein synthesis from polymerase chain reaction-generated templates to study interaction of *Escherichia coli* transcription factors with core RNA polymerase and for epitope mapping of monoclonal antibodies", The Journal of Biological Chemistry, 1991, pp. 2632-2638, vol. 266, No. 4.
Bloemberg et al., "Simultaneous imaging of Pseudomonas fluorescens WCS365 populations expressing three different autofluorescent proteins in the rhizosphere: new perspectives for studying microbial communities", Molecular Plant-Microbe Interactions, 2000, pp. 1170-1176, vol. 13, No. 11.
Sperow et al., "Yeast inorganic pyrophosphatase. VI. Studies on specificity and mechanism", The Journal of Biological Chemistry, 1973, pp. 2062-2065, vol. 248, No. 6.
Ryckelyncl et al., "Using droplet-based microfluidics to improve the catalytic properties of RNA under multiple-turnover conditions", RNA, 2015, p. 458-469, vol. 21, No. 3.
Dorozhkin et al., "Self-setting calcium orthophosphate formulations", Journal of Functional Biomaterials, 2013, pp. 209-311, vol. 4, No. 4.
Yata et al., "Efficient amplification of self-gelling polypod-like structured DNA by rolling circle amplification and enzymatic digestion", Scientific Reports, 2015, 14979, vol. 5.
Roh et al., "A Multi-RNAi Microsponge Platform for Simultaneous Controlled Delivery of Multiple Small Interfering RNAs", Angewandte Chemie International Edition, 2016, pp. 3347-3351, vol. 55, No. 10.
Frenkiel-Krispin et al., "Regulated phase transitions of bacterial chromatin: a non-enzymatic pathway for generic DNA protection", The EMBO Journal, 2001, pp. 1184-1191, vol. 20, No. 5.
Sidore et al., "Enhanced sequencing coverage with digital droplet multiple displacement amplification", Nucleic Acids Research, 2016, e66, vol. 44, No. 7.
Zubaite et al., "Droplet Microfluidics Approach for Single-DNA Molecule Amplification and Condensation into DNA-Magnesium-Pyrophosphate Particles", Micromachines, pp. 1-13, vol. 8, No. 2, 62.
Roh et al., "Layer-by-Layer Assembled Antisense DNA Microsponge Particles for Efficient Delivery of Cancer Therapeutics", ACS Nano, 2014, pp. 9767-9780, vol. 8, No. 10.
Jang et al., "Design of a platform technology for systemic delivery of siRNA to tumours using rolling circle transcription", Nature Communications, 2015, pp. 1-12, vol. 6, Article No. 7930.
International Search Report, dated Jul. 7, 2017, from corresponding PCT application No. PCT/IB2017/050124.

\* cited by examiner

SYSTEM AND METHOD FOR SYNTHESIS OF DNA PARTICLES AND USE THEREOF

SEQUENCE LISTING

The text file named Sequence_Listing.txt, created on Jan. 4, 2021, and sized 645 bytes, which contains sequence ID listings, is herein expressly incorporated by reference.

FIELD OF THE INVENTION

The present invention generally relates to amplification of single DNA molecules into DNA particles (spherulite, hydrogel, crystalline-like structures) and use of amplified DNA material for in vitro transcription and/or translation, gene expression, protein synthesis, imaging, drug delivery and/or other applications.

BACKGROUND OF THE INVENTION

Single DNA molecule compartmentalization and amplification inside nano- or pico-liter sized wells[1] and droplets [2] has opened new opportunities for biomedical and biological sciences. The discrete nature of compartments enables digital quantification of absolute numbers of nucleic acids in a sample[3], accurate estimation of copy number variation[4], detection of pathogens[5] and biomarkers[6] or rare cancer mutations[7], as well as other applications.[8] The most common method of amplifying DNA in a sample involves the polymerase chain reaction (PCR), however, amplification of long (>1 kb) templates is often inefficient, leading to reduced reaction yields. Contrary, DNA amplification under isothermal reaction conditions has been shown to generate large amounts of material from a single copy DNA template [9]. Various isothermal amplification methods exist as reviewed elsewhere [10]. The ability not only to amplify single DNA molecules but also to express proteins from the clonally amplified template will greatly increase the scope of potential applications. For example, synthetic biology, directed evolution and large-scale proteomics screens would benefit from techniques that do not rely on protein expression using living systems. However, a major challenge for in vitro expression of proteins is the relatively large amounts of DNA template needed—on the order of 0.5-500 ng DNA ($10^{\wedge}6$-$10^{\wedge}9$ gene copies) per 50 μL reaction [11-13]—since protein synthesis from a single DNA copy is rather inefficient. An alternative approach is to compartmentalize single DNA molecules in droplets and perform clonal DNA amplification followed by the in vitro transcription-translation (IVTT) reaction have been reported [14]. However, the need for sophisticated microfluidic chips to perform complex droplet manipulations (such as droplet fusion) restricts broader use and further applications. In addition, to date only limited efforts have been made to express proteins from the condensed DNA structures. For example, condensed DNA structures, in the form of hydrogels, have been shown to increase RNA and protein yields in vitro[15], but the synthesis of this type of DNA material is based on ligation and gelation rather than on clonal amplification.

SUMMARY OF THE INVENTION

Here we report a system and method for amplification of single DNA molecules into condensed DNA structures (macromolecules, particles) carrying multiple copies of clonally amplified DNA template and their use as a material for gene expression, transcription, protein synthesis, imaging, drug delivery amongst other applications. To exemplify the use the invention we employed droplet microfluidics approach to convert single DNA molecules into DNA particles by a multiple displacement amplification (MDA) reaction driven by phi29 DNA polymerase. DNA particles were also generated in bulk by performing MDA reaction in 1.5 mL tubes, 96-well or 384-well plates. We show that inorganic pyrophosphate and magnesium ions are a prerequisite for DNA condensation into the crystalline-like globular structures. We found that during MDA reaction the magnesium ions from the buffer and DNA synthesis (replication) reaction byproduct—inorganic pyrophosphate ($PP_i$) precipitates into insoluble and heat-resistant $Mg_2(PP_i)$ spherulitic particles [16, 17] that potentially may act as a seed (nucleus) for the condensation of newly synthesized DNA strands into DNA particle. According to the DNA condensation theory [18], magnesium ions chelated by inorganic pyrophosphate should decrease electrostatic repulsion between the newly synthesized DNA strands thereby facilitating self-assembly into a crystalline structure. The resulting DNA:Mg:$PP_i$ particles can be purified from reaction mix using different means, and still retain significant amounts of clonally amplified DNA. In addition, DNA:Mg:$PP_i$ particles can be of different size, typically 100-1300 nm in diameter, and the size can be controlled by changing DNA amplification reaction conditions. To demonstrate the biological functionality of the DNA particles, we applied them in in vitro transcription/translation reactions and observed improved protein and enzyme expression yields relative to standard assay conditions. The system and method of the present invention can be used to generate DNA particles (hydrogels, spherulites, condensed structures etc.), and other type of materials composed of nucleic acid (NA), applicable for gene expression, imaging, drug delivery and other applications.

In one aspect, the invention comprises the method of nucleic acid (NA) molecule(s) amplification and condensation into a particle(s) comprised of multiple copies of an original template.

In another aspect, the invention relates to the use of obtained particle(s) for, but not limited to, gene expression, protein synthesis, imaging, drug delivery, etc.

In another aspect, the invention relates to the synthesis of particles that are composed of NA, magnesium ions and pyrophosphate.

In one exemplary embodiment, the system to produce particle(s) involves isothermal nucleic acid amplification.

In one exemplary embodiment, the single NA molecules are isolated into droplets.

In one exemplary embodiment, the droplets have a size ranging from 1 to 100 μm.

In one exemplary embodiment, droplet generation occurs on a microfluidic device having a cross-junction geometry.

In one exemplary embodiment, the above methods are carried out but not limited to using a microfluidics system.

In one exemplary embodiment, the invention comprises the method for conversion of encapsulated DNA molecule(s) into DNA particle(s).

In one exemplary embodiment, the condensation of DNA is triggered by pyrophosphate and cations.

The cations can but not limited to magnesium, calcium and other molecules.

In one exemplary embodiment, the DNA macromolecules are released from the emulsion by braking emulsion (de-emulsification). Typically, but not limited to, emulsion can broken by chemical means, temperature or electric field by destabilizing the water-oil interface.

In another exemplary embodiment single DNA molecule(s) are converted into DNA particle(s), without involving droplets.

In another exemplary embodiment amplified DNA molecule(s) forms condensed globular macrostructure often referred as nanoparticle, spherulite, DNA nanoflower, DNA nanoball, DNA hydrogel and others. Herein, macromolecule and nanoparticle terms are used interchangeably to describe nucleic acid material that has size larger than 100 nm irrespectively of the shape, structure or term used in the literature.

In another exemplary embodiment, DNA macromolecule(s) are purified from the reaction mix.

In one exemplary embodiment, the invention described the use of DNA particle(s), but not limited to, gene expression, protein synthesis, imaging, etc.

In another exemplary embodiment, DNA macromolecule(s) can be used to increase the yields of in vitro transcription/translation reaction.

$$\left(1 - \frac{\lambda^k e^{-\lambda}}{k!}\right) \times 100\%,$$

where e is a constant equal to 2.718, λ is an average (mean) number of DNA molecules per one droplet and k is equal to 0. The fraction of droplets that are occupied by DNA molecules was obtained by estimating the number of empty droplets and subtracting the obtained value from 1. The Poisson function is plotted as a blue line, black circles denote theoretical occupancy values for a given lambda, and the purple squares denote experimentally determined occupancy values for the same lambda values. The small difference between the theoretical prediction and experimental results (root mean square, RMS=7.9) can be attributed to dilution errors, DNA losses due to non-specific adsorption, damaged DNA molecules or other factors.

Figure 3:
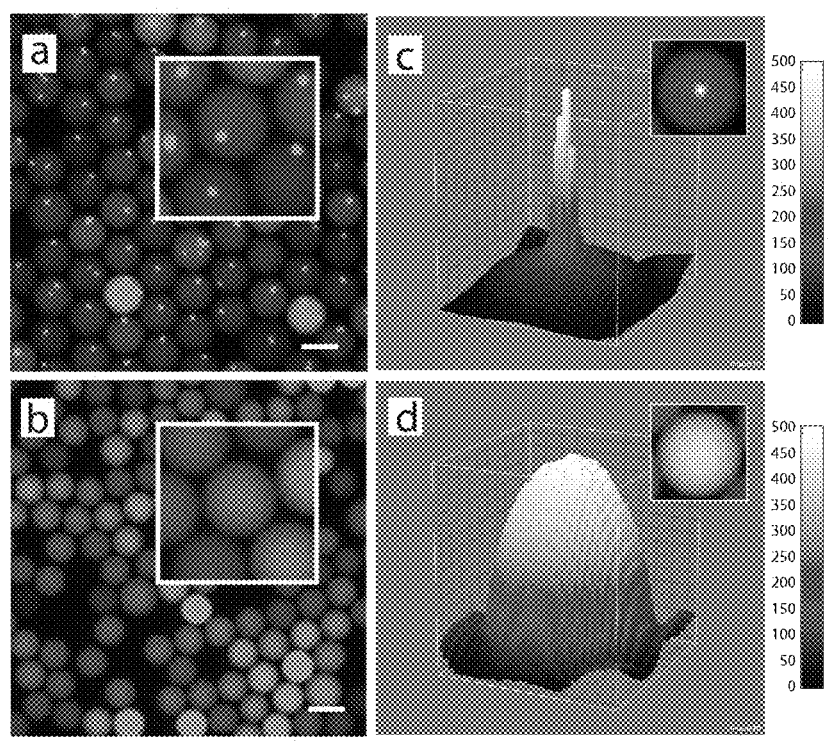

FIG. 3. DNA nanoparticle generation. (a) DNA nanoparticle formation induced by inorganic pyrophosphate and magnesium ions during a phi29-catalyzed polymerization reaction in the absence of the pyrophosphatase enzyme. For visualization purposes the initial DNA template concentration was chosen at λ~1.0, and as a result small fraction of droplets appears with ≥2 DNA particles. (b) The same reaction as in panel a, but with pyrophosphatase. Insets show a magnified view of the emulsion; the DNA nanoparticles are evident as localized and intensely fluorescent objects within the droplets. Scale bars denote 20 μm. The composition of reaction mixtures is described in the Material and Methods section. (c) A 3D fluorescence intensity profile of a single droplet containing a single DNA nanoparticle. (d) A 3D fluorescence intensity profile of a droplet with ~$10^5$ copies of a DNA template. Color bars indicate an approximate DNA copy number per single pixel (0.66 μm size).

Figure 4:
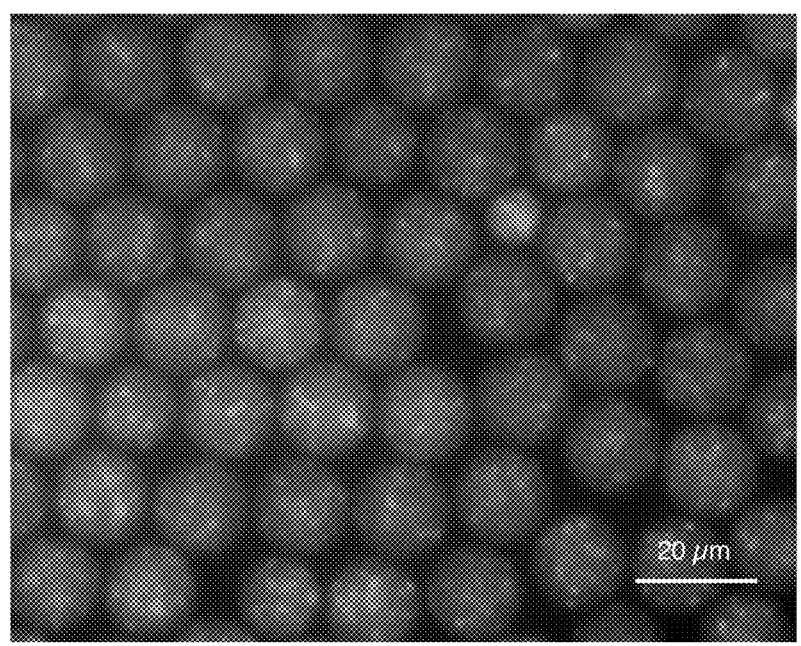

FIG. 4. DNA precipitation in the presence of inorganic pyrophosphate and magnesium chloride. pUC19 DNA at 0.23 μM concentration (λ=4·$10^5$) was dissolved in 8 mM Tris-HCl buffer [pH 7.6] containing 4 mM sodium pyrophosphate and 10 mM $MgCl_2$. Reaction mix was encapsulated into microfluidic droplets, stained with SYBR Green I dye, and fluorescence recorded after 30 min of incubation at 22° C.

Figure 5:
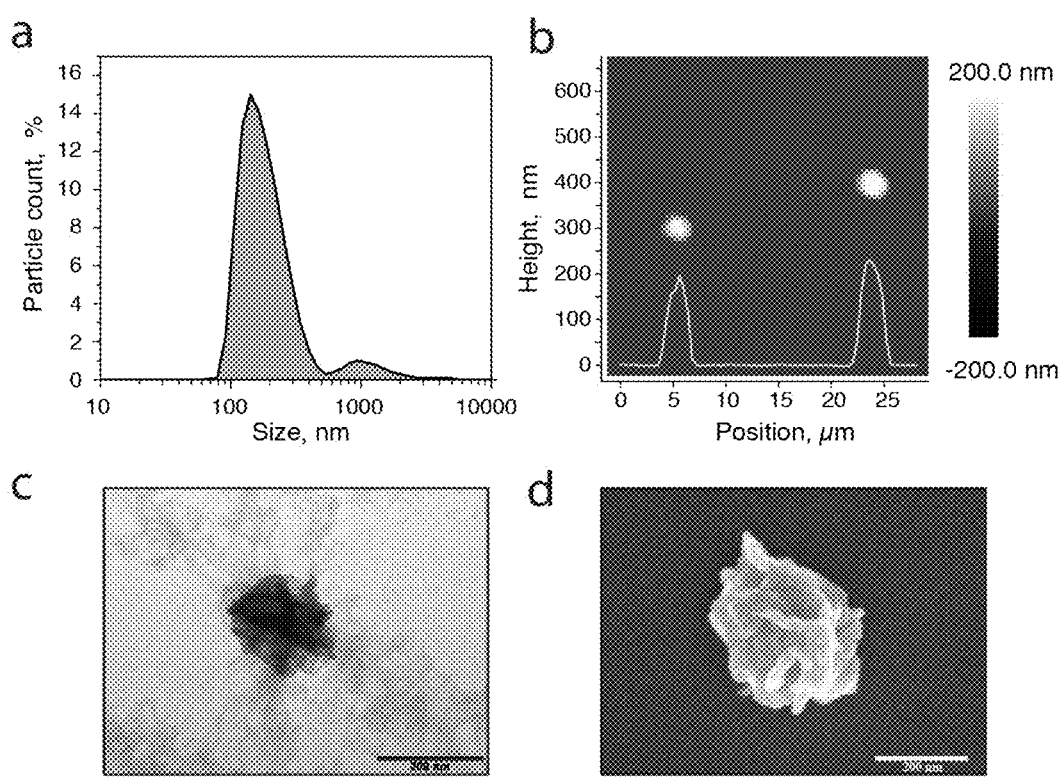

FIG. 5. DNA nanoparticle characterization. (a) Dynamic light scattering measurements, showing that 93.5% of the particles have 152±37 nm diameters. (b) Atomic force microscopy measurements on two representative DNA nanoparticles. The size of the DNA nanoparticles was estimated to be ca. 200 nm (yellow trace over-layered over AFM image). (c) Transmission electron microscopy and (d) scanning electron microscopy images of single DNA nanoparticles. Scale bars, 200 nm.

Figure 6:
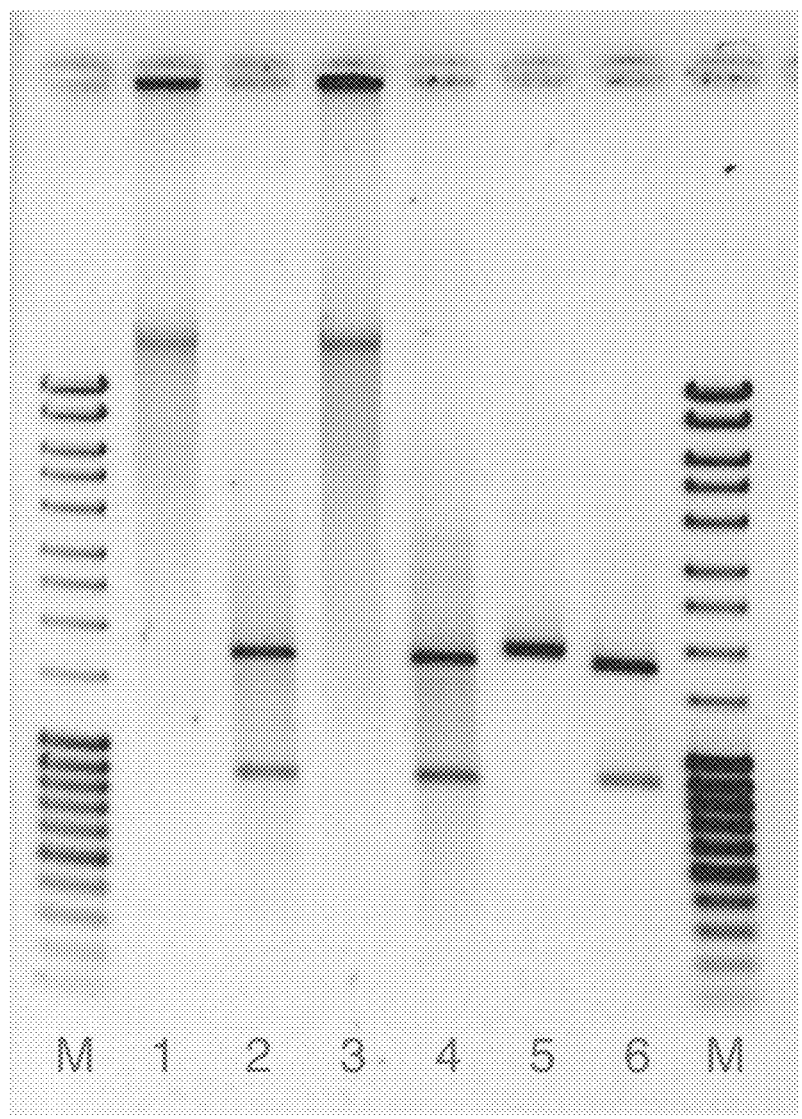

FIG. 6. Electrophoretic analysis of amplified DNA. pUC19 plasmid DNA was amplified using standard phi29 reaction conditions with or without pyrophosphatase (PPase) as described in the Materials and Methods section. The amplified DNA was released from droplets, digested with Fast Digest PvuI restriction endonuclease, diluted 5-times in 1×DNA Loading Dye and run in a 1% agarose gel at 5.5 V/cm in TAE buffer (40 mM Tris HCl [pH 8.0], 20 mM Acetic acid and 1 mM EDTA). The gel was stained with 0.5 mg/ml of ethidium bromide in TAE buffer.

Lane M: DNA ladder (MassRuler DNA Ladder, #SM0403);
Lane 1: Amplified DNA without PPase
Lane 2: Amplified DNA without PPase and digested with PvuI
Lane 3: Amplified DNA with PPase
Lane 4: Amplified DNA with PPase and digested with PvuI
Lane 5: Native pUC19 plasmid
Lane 6: Native pUC19 plasmid digested with PvuI FIG. 7. Transmission electron microscopy image of amplified DNA in droplets (a) and in bulk (b). Single DNA plasmid molecules amplified in microfluidic droplets using MDA reaction led to formation of densely packed DNA particles (a). In contrast, amplified DNA material generated in bulk (b) using the same reaction conditions as in panel (a) produced loose DNA aggregates without clearly pronounced structure. The composition of reaction mix is described in the Material and Methods section. Scale bars denote 200 nm top row, and 2000 nm bottom row.

Figure 8:
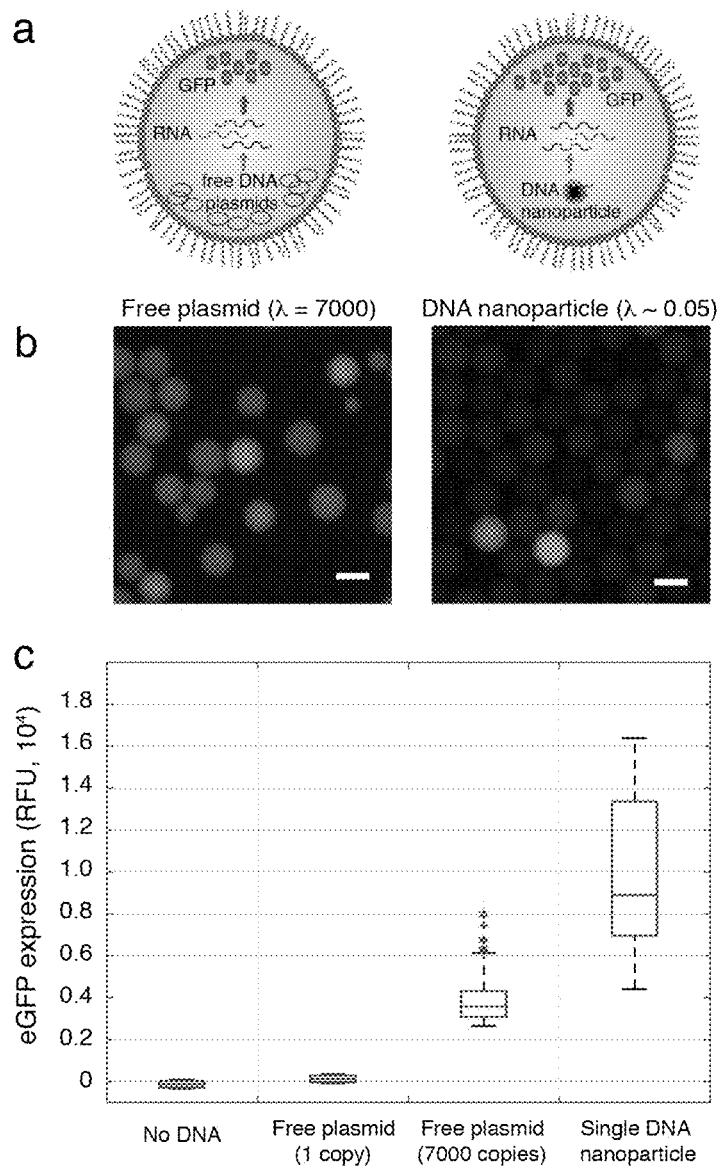

FIG. 8. In vitro transcription-translation (IVTT) reaction. (a) Schematic of an IVTT reaction carried out in droplets. (b) Fluorescence images of an IVTT emulsion prepared with free DNA plasmid at λ~7000 (left) and DNA nanoparticles at λ~0.05 (right). For visualization purposes, droplets containing plasmids were mixed with droplets lacking DNA. The latter showed no fluorescence and appear as dark droplets interspersed among bright droplets. Scale bar, 20 μm (c) The median yield of eGFP expression. The results are plotted as a box-plot, where median is shown as a red line.

The statistical significance of eGFP expression differences for droplets containing free plasmid (7,000 copies of the template) and a single DNA nanoparticle (carrying ~6,000 copies of the template) was determined using the Student's t-test (P=3.2·10$^{-9}$).

Figure 9:
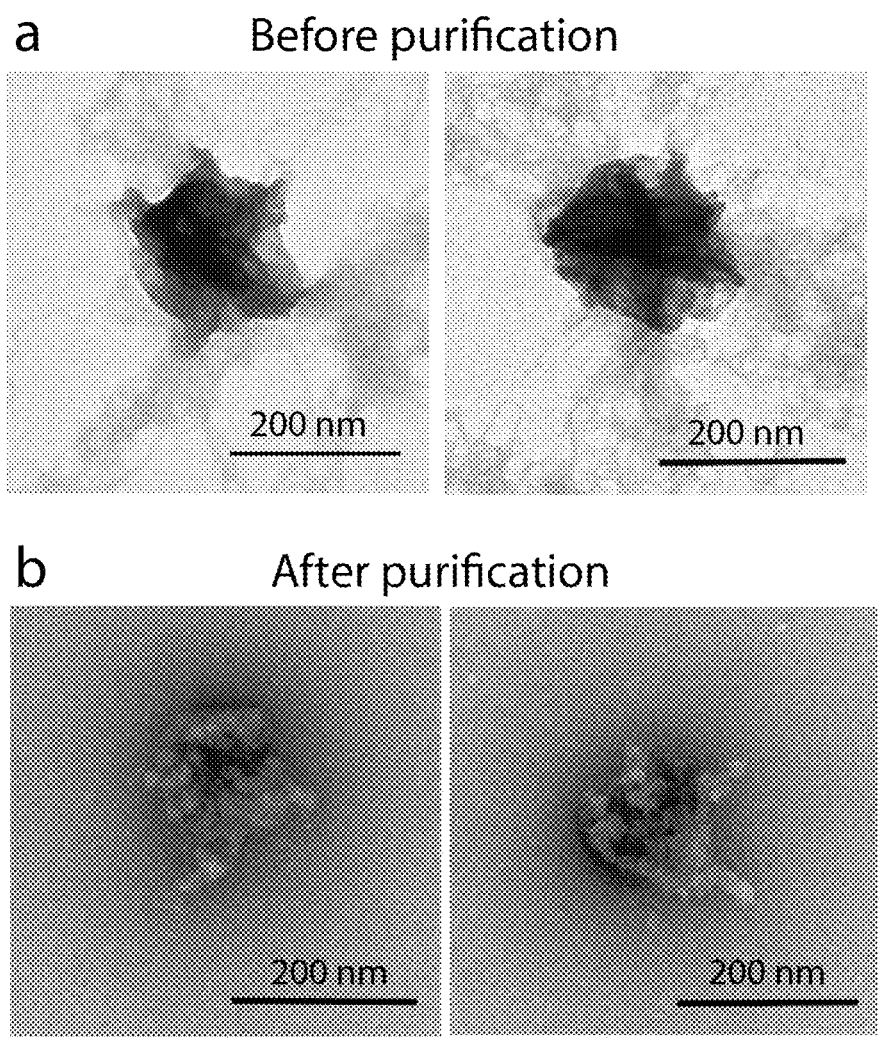

FIG. 9. Transmission electron microscopy images of the individual DNA particles. DNA particles were synthesized in microfluidic droplets as described in the main text and Material and Methods section. (a) TEM image of representative DNA particles before purification. (b) TEM image of representative DNA particles after purification via preparative agarose gel electrophoresis.

Figure 10:
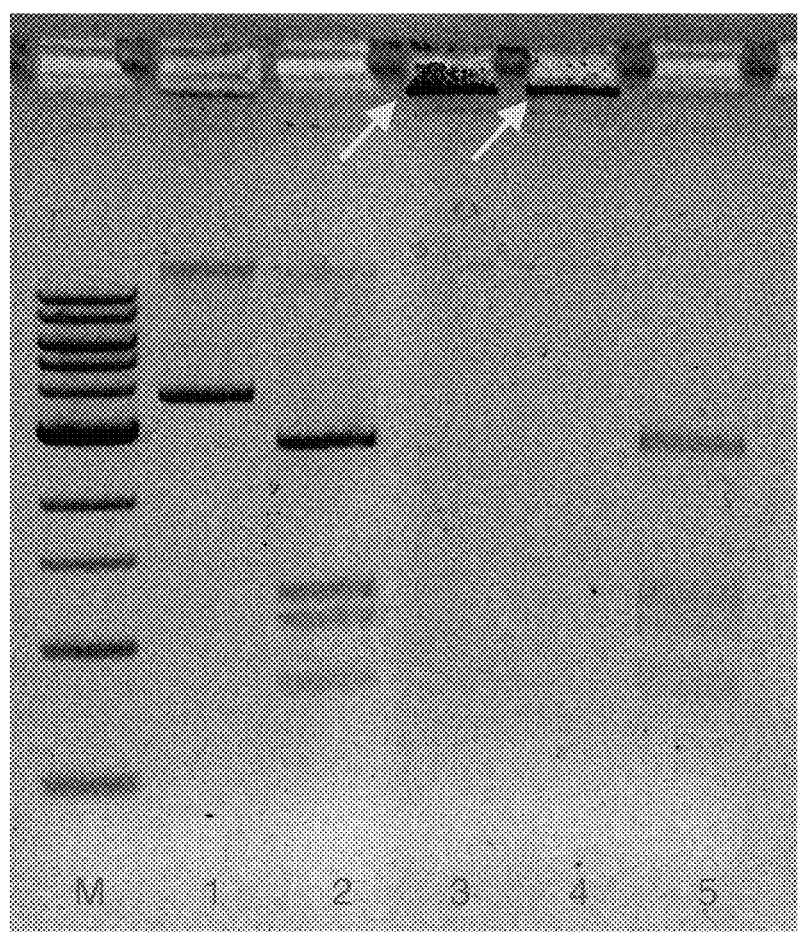

FIG. 10. Electrophoretic analysis of DNA particles. DNA particles were synthesized as described in the main text. After DNA amplification, the reaction product released from droplets was analyzed on a 1% agarose gel and compared to the native DNA plasmid. Applied voltage was 5.5 V/cm.
Lane M: DNA ladder (1 kb DNA ladder, NEB);
Lane 1: native pET29-eGFP plasmid;
Lane 2: pET29-eGFP plasmid digested with BanII restriction endonuclease;
Lane 3: DNA particles (note that nearly all material remains inside the well as indicated by the yellow arrow);
Lane 4: the same sample as in lane 3 but pre-incubated for 1 hour at 37° C., showing that the DNA particles are stable and not degraded in the absence of nucleases (arrow);
Lane 5: DNA particle treated with BanII restriction endonuclease for 1 hour at 37° C. Note that the digestion products migrate the same distance as native plasmid (lane 2).

Figure 11:
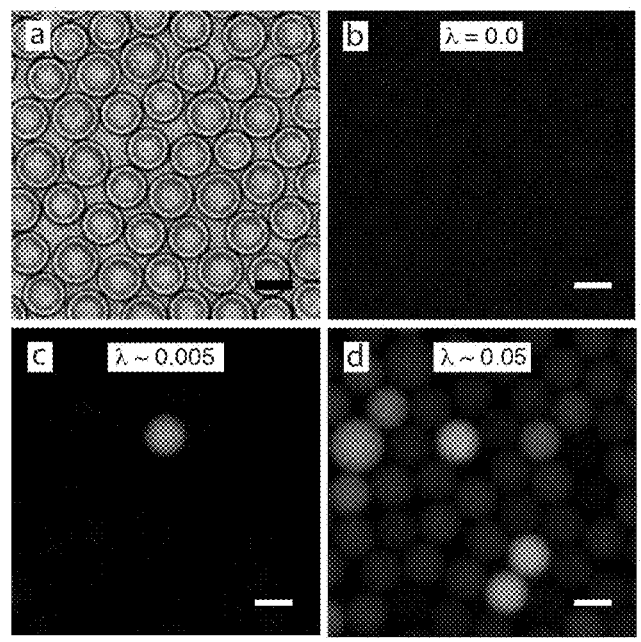

FIG. 11. In vitro transcription/translation reaction using purified DNA particles. DNA particles were encapsulated in 5 pL droplets with IVTT mix at different dilutions and eGFP expression levels were analyzed by measuring green fluorescence. Bright field of an IVTT emulsion is indicated in panel (a). Fluorescence images of an IVTT emulsion prepared with DNA particles at $\lambda$=0.0 (b), $\lambda$~0.005 (c) and $\lambda$~0.05 (d) are shown. Scale bars denote 20 μm.

Figure 12:
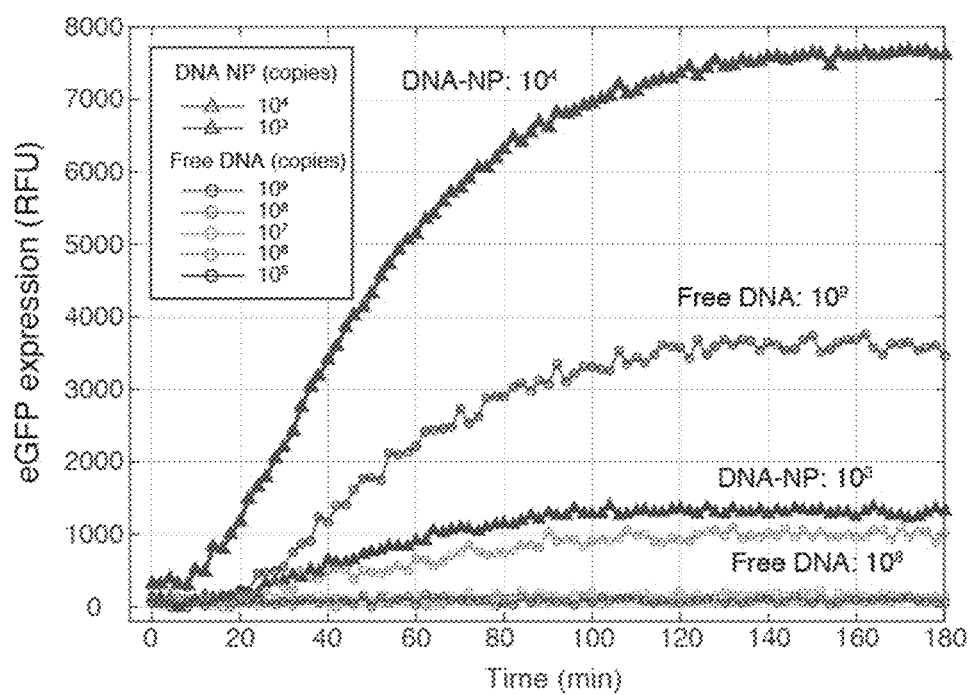

FIG. 12. IVTT reaction in bulk using different dilutions of pET29-eGFP plasmid (10$^9$-10$^5$ copies in 10 μL IVTT reaction). The corresponding amount of plasmid DNA (Free DNA) and DNA nanoparticles (DNA-NP) is indicated in the top corner of the graph. The number of eGFP gene copies in a single DNA nanoparticle was approximately 6,000, yet the yields of in vitro synthesized protein was significantly higher (blue triangles) as compared to the sample containing similar amount of free DNA (red circles).

Figure 13:
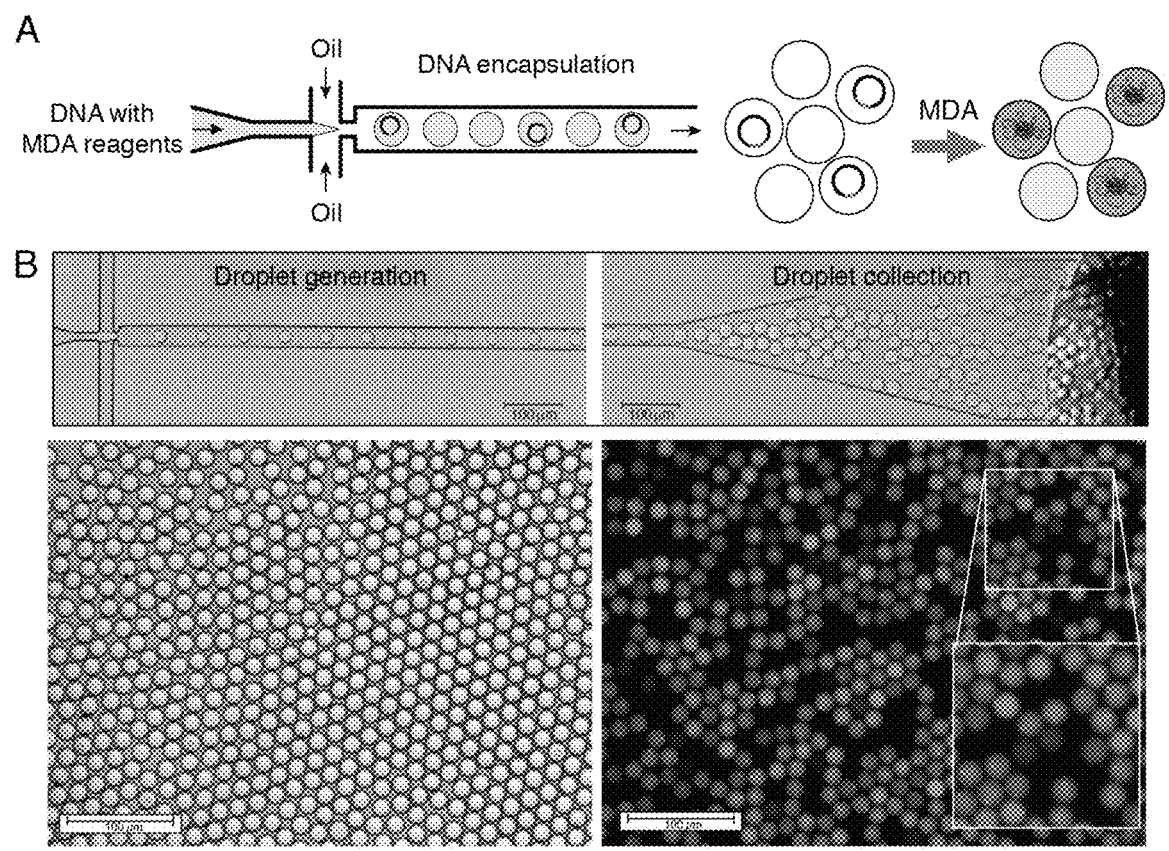

FIG. 13. Another example of DNA encapsulation and amplification using droplet microfluidics. (A) Schematic representation of single DNA molecule isolation and condensation into DNA particles. (B) Top: still images showing droplet generation and collection. Bottom: the bright field and fluorescence micrographs showing emulsion droplets after MDA reaction. The bright fluorescent objects are visible in droplets. Scale bars, 100 μm.

Figure 14:
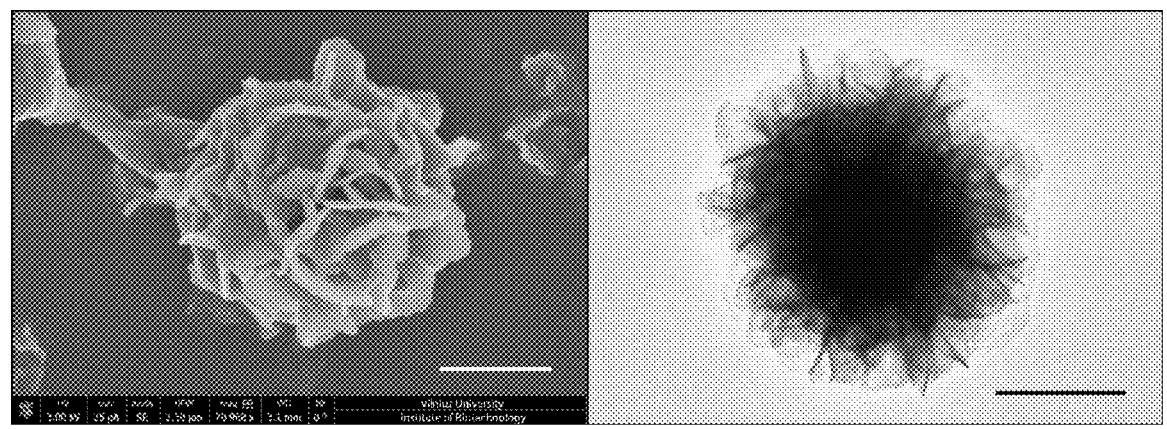

FIG. 14. Electron microscopy analysis of ~1000 nm size DNA:magnesium:pyrophosphate particles produced during multiple displacement amplification reaction. Scanning electron microscopy (left) and transmission electron microscopy (right) images of a DNA:Mg:PP$_i$ particle produced in 3 pl droplet during MDA reaction. Scale bars denote 1 μm.

Figure 15:
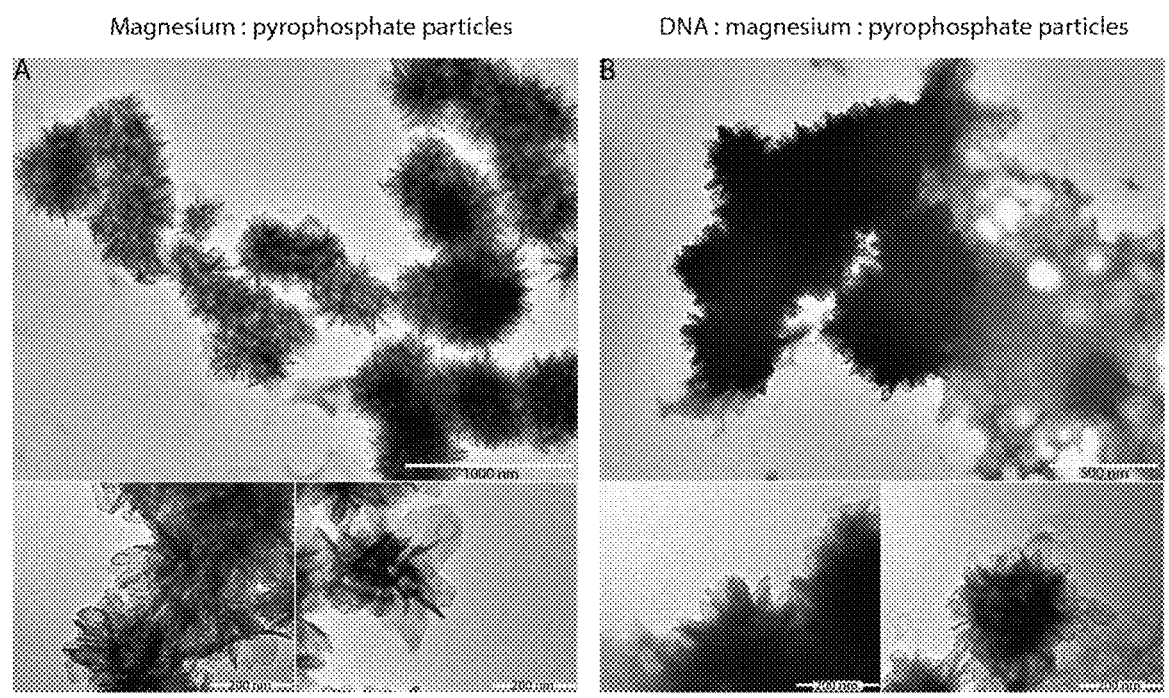

FIG. 15. Transmission electron microscopy images of magnesium:pyrophosphate and DNA:magnesium:pyrophosphate particles produced in bulk by mixing individual components. The particles were produced in bulk by mixing individual components. (A) Inorganic magnesium-pyrophosphate particles produced by mixing 10 mM MgCl$_2$ and 5 mM sodium pyrophosphate (Na$_4$P$_2$O$_7$) in deionized water. (B) Particles from panel A mixed with 56 nM plasmid DNA (300 ng/μl) and imaged under TEM. Denser staining with uranyl acetate suggests DNA adsorption. No DNA amplification was involved.

Figure 16:
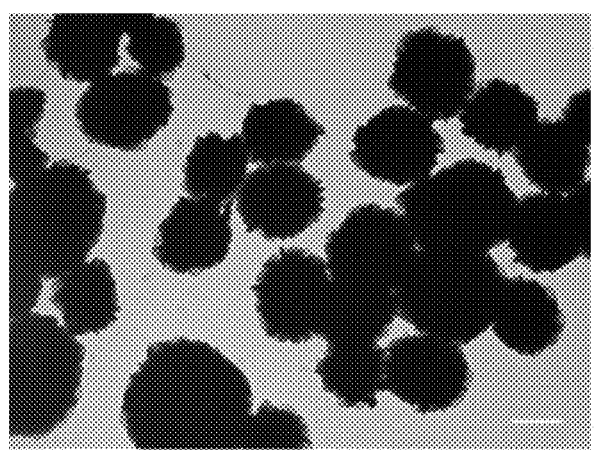

FIG. 16. TEM image of purified DNA:magnesium:pyrophosphate particles. DNA particles produced during MDA reaction were released from droplets, digested with diluted restriction endonuclease enzyme and purified by centrifugation followed by TEM imaging. Scale bar, 1 μm.

Figure 17:
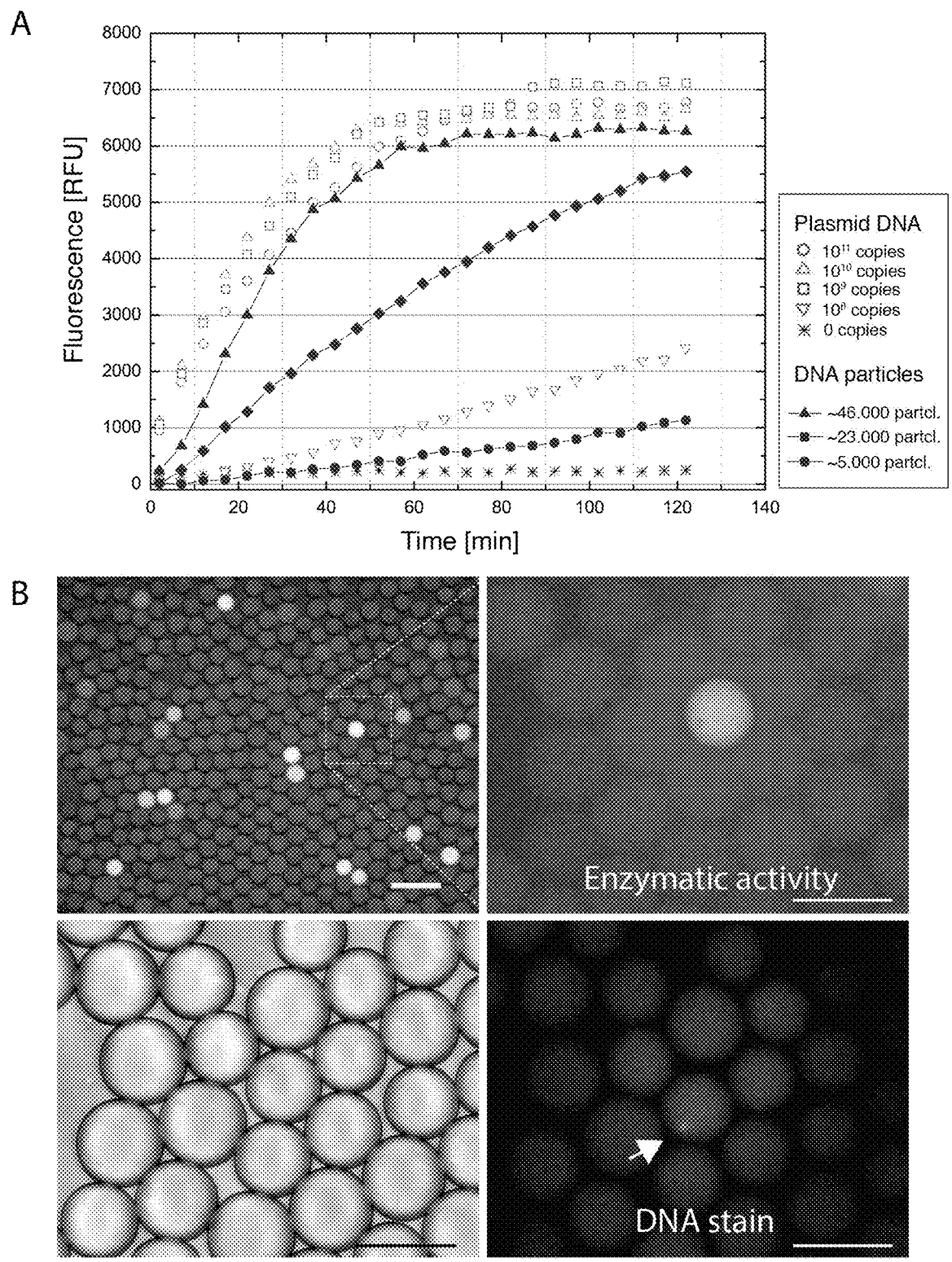

FIG. 17. lacZ expression in vitro using purified DNA:magnesium:pyrophosphate particles as a template. (A) Evaluation of the catalytic activity of the in vitro synthesized β-galactosidase enzyme. Protein synthesis was performed in a 384-well format using different dilutions of pIVEX-lacZ-his plasmid (10$^{11}$-10$^8$ copies in 10 μl IVTT reaction) and purified DNA:Mg:PP$_i$ particles (approximately 46.000, 23.000 and 5.000 particles in 10 μl IVTT reaction). The corresponding amount of plasmid DNA and DNA particles is indicated on the right side of the graph. Solid symbols indicate enzymatic activity of lacZ protein synthesized from the DNA particles, whereas open symbols indicate protein synthesized from the plasmid DNA. (B) Evaluation of IVTT reaction and enzymatic activity in droplets. Purified DNA particles were encapsulated in 18 pl droplets ($\lambda$~0.1) and lacZ expression levels were measured by the accumulation of fluorescent product (fluorescein). To visualize DNA particles in droplets the DNA stain (ethidium bromide) was used. Scale bars denote 50 μm.

Figure 18:
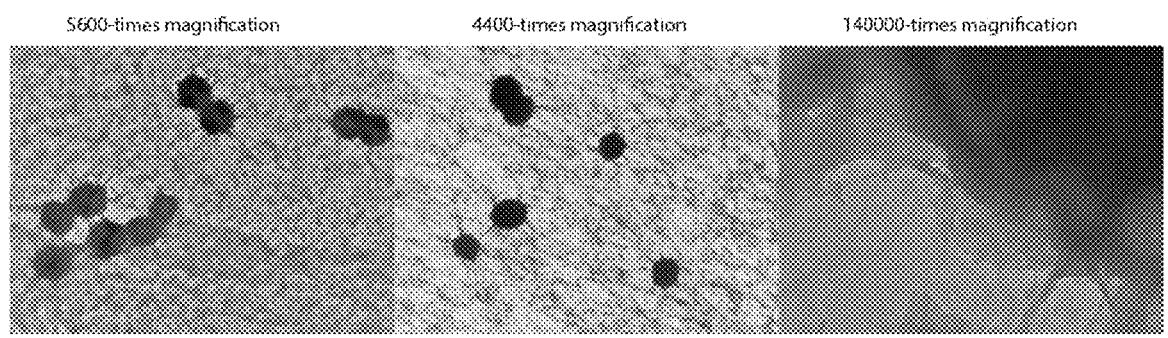

FIG. 18. Transmission electron microscopy images of DNA particles produced in bulk (tube containing 50 μL reaction volume) during MDA reaction. MDA reaction mix contained pUC19 DNA plasmid ~0.001 ng/uL, random hexamer primers 10 Pluronic F127 0.4% (w/v), dNTPs 1 mM, 1×phi29 polymerase buffer and phi29 DNA polymerase 0.8 U/uL.

DETAILED DESCRIPTION OF THE INVENTION

The present invention firstly provides a method for amplifying single DNA molecules into large molecular weight DNA structures (macromolecules, nanoparticles), DNA condensation in the present of pyrophosphate and magnesium or calcium ions, and the use DNA nanoparticles for gene expression, protein synthesis, imaging and other applications.

The term "nanoparticle" or "particle" or "macromolecule" are used interchangeably, and herein refers to a single or plurality of nucleic acid molecules that form a structure of size larger than 10 nm.

In an embodiment, the DNA is amplified enzymatically using isothermal amplification.

In a more particular embodiment, single DNA molecules are isolated into droplets and amplified using multiple displacement reaction.

In yet another embodiment, single DNA molecules are not isolated into droplets and are amplified using multiple displacement reaction in bulk format (tubes, 96-well or 384-well plate).

Microfluidic device may be used to isolate and compartmentalize DNA molecules. Microfluidic device, or chip, as used herein, refers to a microdevice of only millimeters to a few square centimeters or tens of centimetres in size dealing with the handling of extremely small fluid volumes down to less than femto liters. Microfluidic chips are usually fabricated by using lithography-based technologies such as soft lithography. For example FIG. 1 exemplified microfluidics device.

In the method of the invention, the microfluidics chip comprises, but not limited to, following units:
(i) an inlet and microfluidic channel(s) for carrier oil;
(ii) an inlet and microfluidic channel(s) for the first fluid;
(iii) an inlet and microfluidic channel(s) for the second fluid;
(iv) an inlet and microfluidic channel(s) for the third fluid;
(v) a nozzle;
(vi) a microfluidics channel connecting the nozzle with the outlet, and
(vii) collection outlet.

In an embodiment, the fluids are introduced into the microfluidics chip via an inlet(s) and passes through the passive filter(s) and fluid resistor(s).

In the method of the invention, the DNA particles are produced inside the droplets. For example, FIG. 2a shows DNA particle formation in the presence of pyrophosphate.

In the method of the invention, the DNA condensation into a particle can be triggered by the presence of pyrophosphate and magnesium ions. For example, FIG. 3 shows DNA precipitations in the presence of pyrophosphate and magnesium ions.

In an embodiment, the size of DNA particles have a diameter ranging from 10 nm to 10,000 nm and more preferably from 100 nm to 2000 nm. The size of DNA nanoparticle produced during isothermal amplification can be controlled by the amplification time, enzyme amount, dNTP concentration, magnesium and pyrophosphate amount, or other additives.

In an embodiment, the DNA nanoparticles are produced during isothermal DNA amplification reaction.

In a particular embodiment, DNA nanoparticles are produced using phi29 DNA polymerase.

In a more particular embodiment, DNA nanoparticles are produced using multiple displacement reaction.

In a first embodiment, the DNA nanoparticles are first produced in droplets and then are released from the droplets by breaking the droplets.

In a second embodiment, the DNA particle(s) are produced in standard laboratory tube or microtiter plate without using droplets.

The DNA particle(s) preserves (at least partly) their compact structure during purification procedure.

The purified DNA particle(s) preserves large number of copies of an original template.

In an embodiment, the number of gene copies in a single DNA particle is larger than one.

In a preferred embodiment, the number of gene copies in a single DNA particle is larger than 10, in a more preferred embodiment the number of gene copies in a single DNA particle is larger than 100, in even more preferred embodiment the number of gene copies in a single DNA particle is larger than 1000.

In a first embodiment the DNA particle(s) are employed as a template for in vitro transcription/translation reaction.

In a second embodiment, in vitro transcription/translation reaction using DNA particles as a template produce high yields of protein.

In a further embodiment, the method of the invention further comprises the use of DNA particles for directed evolution, drug delivery, synthetic biology, proteomics, high-throughput screening and other applications.

The following example is given for purposes of illustration and not by way of limitation.

EXAMPLE

Materials and Methods
DNA and Oligonucleotides

The gene encoding enhanced GFP (eGFP) was subcloned from pMP4655[19] into the commercial pET-29b(+) vector (Novagen) using NdeI and XhoI restriction endonuclease sites. Primers for subcloning (forward primer: 5'-TAA TAA CAT ATG GTG AGC AAG GGC G (SEQ ID NO: 1) and reverse primer: 5'-TTA TTA CTC GAG CTT GTA CAG CTC G (SEQ ID NO: 2)) were purchased from Microsynth AG. pET29-eGFP plasmid was isolated from an overnight *Escherichia coli* XL1-blue cell culture using the "ZR Plasmid Miniprepm ™-Classic" kit (Zymo Research). Plasmid concentration was determined using a "Nanodrop" spectrometer (Thermo Scientific) and confirmed densitometrically in 1% agarose gel by comparing with a DNA mass standard (New England Biolabs (NEB), 2-Log DNA Ladder). The pUC19 plasmid was from Thermo Scientific. Random exo-nuclease resistant heptanucleotide primers were purchased from Thermo Fisher Scientific and Microsynth. The presence of two phosphorothioate groups at the 3' end of the primer confers resistance to 3'→5' exonuclease activity. The pIVEX2.1-lacZ-his plasmid encoding lacZ protein was used to express enzyme β-galactosidase.

Microfluidic Chip Fabrication and Operation.

The microfluidic device was fabricated following soft-lithography protocol as previously described[20]. Rectangular microfluidic channels were fabricated using soft lithography by pouring poly(dimethylsiloxane) (PDMS, Sylgard 184, Dow Corning Corp.) onto a positive-relief silicon wafer (SILTRONIX) patterned with SU-8 photoresist (Microchem Corp). Curing agent was added to PDMS base to a final concentration of 10% (w/w), degassed and poured over the mould for crosslinking at 65° C. for 12 hours. The structured PDMS layer was peeled off the mould and the inlet and outlet holes were punched with a 0.75 mm-diameter Harris Uni-Core biopsy punch (Electron Microscopy Sciences). The microchannels were sealed by bonding the PDMS to glass using an oxygen plasma (PlasmaPrep 2 plasma oven; GaLa Instruemente GmbH). The channels were treated with surface coating agent Aquapel to make it hydrophobic and subsequently flushed with nitrogen. Each of the fluids were injected into the PDMS channels via PTFE tubing (Fisher) connected to 1 mL syringes (Omnifix-F®) and Neolus needles (Terumo). The flow rates of liquids and oil were controlled by syringe pumps (PHD 2000, Harvard Apparatus). The rectangular microfluidic channels were 10 µm deep and allowed production of 2 to 8 pL droplets by adjusting the flow rates of the aqueous and oil phases. Typical flow conditions were 50 µL/h for the dispersed phase and 150 µL/h for the continuous phase. The HFE-7500 fluorinated oil (3M) containing 2% (w/v) EA-surfactant (RainDance Technologies) was used as the continuous phase. During encapsulation, samples were kept at 4° C. using ice-cold jacket. The emulsion was collected in a 0.2 mL thin walled PCR tube (Eppendorf) placed in an ice rack. To prevent water loss due to evaporation, the emulsion was collected in a tube prefilled with 80 µL of mineral oil (Sigma).

DNA Nanoparticle Release from Droplets

To release DNA nanoparticles from emulsion PFO was added on top of emulsion and incubated at room temperature for 5 min. The supernatant containing DNA nanoparticles was then analyzed accordingly.

DNA Amplification.

Figure 1:
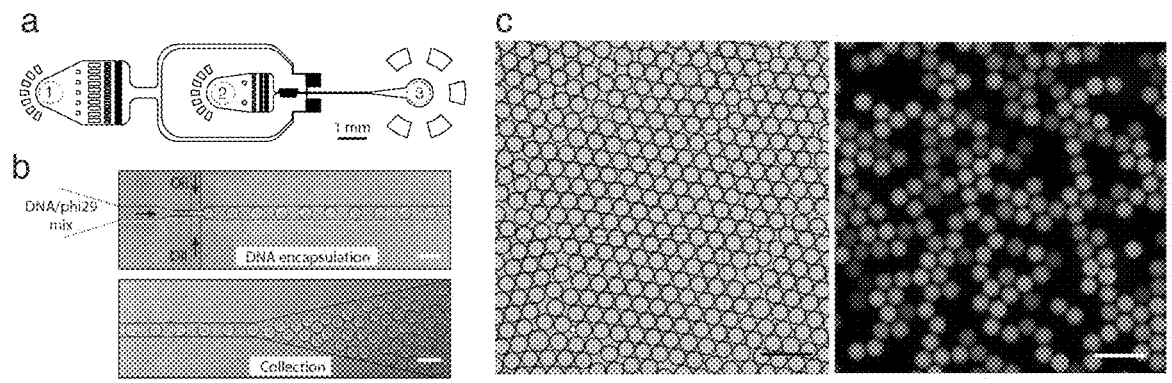
FIG. 1: Design and operation of the microfluidics device. (a) The microfluidics device, showing the inlet for the continuous phase 1, the inlet for the MDA reaction mix 2, and the droplet collection outlet 3. (b) Still images of droplet production and collection. (c) Bright field and fluorescence images of an emulsion after an MDA reaction. Droplets containing amplified DNA exhibit green fluorescence, whereas droplets lacking a template are dark. Scale bars, 50 μm.

All reaction components were from Thermo Fisher Scientific unless stated otherwise. The standard DNA amplification reaction mix contained from 0.0001 to 100 ng/µL pET29-eGFP plasmid, 1×phi29 polymerase reaction buffer (33 mM Tris-acetate [pH 7.9], 10 mM Mg-acetate, 66 mM K-acetate, 0.1% (v/v) Tween 20, 1 mM DTT), 50 µM exo-nuclease resistant heptanucleotide primers, 0.2 mM of each dNTP, 0.4% (w/v) Pluronic F-127, 0.005 U/µL pyrophosphatase and 0.2 U/µL phi29 DNA polymerase. The enriched reaction mix contained 0.8 U/µL phi29 DNA polymerase and 1 mM of each dNTP. The reaction components were mixed in DNA LoBind tubes (Eppendorf) by adding DNA, nuclease free water, pluronic F-127 and heptamers, and then heated to 95° C. for 20 s. Next, the mixture was quickly transferred onto ice and, following addition of the remaining components, encapsulated using the microfluidic device (FIG. 1). The encapsulation step typically took ~15-20 min. The collected emulsion was incubated for 15 hours at 30° C. and then heated at 65° C. for 10 min to inactivate phi29 DNA polymerase.

In another example, the MDA reaction mix contained pIVEX2.1-lacZ-his plasmid, 1×phi29 reaction buffer (33 mM Tris-acetate [pH 7.9], 10 mM Mg-acetate, 66 mM K-acetate, 0.1% (v/v) Tween 20, 1 mM DTT), 50 µM exo-nuclease resistant hexanucleotide primers, 1 mM of each dNTP, 0.4% (w/v) Pluronic F-127 and 0.8 U/µl phi29 DNA polymerase (Thermo Fisher Scientific). The reaction components were mixed in DNA LoBind tubes (Eppendorf) by adding DNA template, nuclease-free water, Pluronic F-127 and hexamers, and then heated to 90° C. for 20 s to allow primer annealing. Next, the mixture was quickly transferred onto ice and, following addition of the remaining components, encapsulated using the microfluidic device (FIG. 13).

Staining of Droplets and Fluorescence Analysis.

After amplification, the emulsion droplets were stained with SYBR Green dye I (Life Tech) by adding 4 µL of 100× dye solution to the carrier oil. During incubation at room temperature for 15 min, the dye passively migrated between the droplets and stained dsDNA. Longer incubations did not affect either the number or intensity of the fluorescent droplets. Fluorescence images were recorded with a 1.5 megapixel digital camera (Ds-Qi1, Nikon) assembled on an inverted microscope (Nikon Ti-U Eclipse) equipped with a mercury lamp (Intensilight, Nikon). Fluorescence excitation was set at 470±20 nm (with a 300 ms exposure) and emitted light collected at 525±25 nm. Recorded images were processed with open-source software Fiji (ImageJ) to count the total number of droplets, the number of fluorescent droplets, mean fluorescence intensity values, and the coefficient of variation.

Tem Imaging.

Transmission electron microscopy images were recorded on an FEI Morgagni 268 instrument. 4 µL sample was placed on a grid (QUANTIFOIL, 100 Formvar/Carbon Films, Cu 400 mesh) and incubated for 1 min at room temperature. After draining excess liquid, the sample was washed twice with MQ-Water, stained with 2% (w/v) uracyl acetate for 20 s, and then imaged. DNA particles were generated during isothermal DNA amplification reaction using 1 pM pET29-eGFP plasmid DNA ($\lambda$=1.86), 0.8 U/µL phi29 DNA polymerase, 1 mM dNTP, 50 µM exo-resistant random hexamers, 0.4% (v/v) Pluronic F-127, 1×phi29 reaction buffer (50 mM Tris-HCl [pH 7.5], 10 mM $MgCl_2$, 10 mM $(NH_4)_2SO_4$, 2 mM DTT), 0.2% (v/v) DMSO and 0.5×SYBR Safe dye.

AFM Imaging.

5 µL sample (~$3 \cdot 10^4$ DNA particles per 1 µL) was diluted in 50 µL imaging buffer (33 mM Tris-acetate [pH 7.9], 10 mM Mg-acetate, 66 mM K-acetate, 0.1% (v/v) Tween 20, 1 mM DTT) and 10 µL deposited on freshly cleaved mica. After 10 min incubation at 22° C. mica surface was washed 3-times with imaging buffer and dried at ambient temperature (22° C.) for few minutes. Measurements were performed in an open atmosphere using BioScope Catalyst (Bruker, USA) instrument. The soft tapping mode was employed using TESP probe at a resonant frequency 320 kHz and spring constant 42 N/m.

DLS Measurements.

Dynamic light scattering measurements were performed on Nano ZS Zetasizer (Malvern Instruments Ltd) equipped with a 4.0 mW laser operating at $\lambda$=633 nm and at a scattering angle 173°, and using Non-Invasive-Back-Scatter (NIBS) mode. The sample was diluted 5-times in 25 mM $MgCl_2$ solution (10 µL sample and 40 µL, 25 mM $MgCl_2$) and measured in triplicate and plotted in FIG. 2. The analysis revealed a major peak at 152±37 nm (mean±standard deviation) and a secondary peak at 1669±645 nm. The 152 nm size particles comprised 93.5% and 1669 nm size particles comprised 6.5% of total particle count.

SEM Imaging.

Scanning electron microscopy was performed on Helios Nanolab 650 (FEI) instrument. DNA particles were released from the droplets and deposited on a silicon wafer pretreated with an oxygen plasma. After 10 min of incubation, sample was washed 3-times with nuclease free water, dried in an open atmosphere for 5 min and sputtered with chrome for 20 s at 120 mA in a magnetron sputter. The DNA particles were imaged at 50,000-100,000 magnification using SE mode, 3.0 kV and 0.25 pA parameters.

DNA Particle Purification.

After the phi29 amplification reaction, samples were mixed with 6×DNA Loading dye and loaded onto an 0.8% low melting point agarose gel (Promega, Analytical grade). DNA material that stayed at the well (yellow arrows in Supplementary Figure S6) was excised with a razor blade. The gel slice was transferred to a DNA LoBind tube and digested with β-agarase I (NEB) according to the manufacturer's recommended protocol. Following addition of 1 µg/mL ethidium bromide to increase the density of the DNA particles, the samples were centrifuged at 17,500 g for 30 min. The precipitate was suspended in nuclease free water and used directly for in vitro protein synthesis.

In another example, after the DNA amplification reaction, samples were digested with restriction endonucleases (RE) for 15 min at 37° C. to remove the loose DNA that has not been incorporated into the DNA particles. The REs were chosen such that they would cleave plasmid once, and outside the encoded gene. 1 U/µl of XagI (EcoNI) was used to cleave DNA particles produced from pET-29b-eGFP plasmid and 1 U/µl of HindIII was used to cleave DNA particles generated from pIVEX2.2EM-lacZ-his plasmid. Following digestion by REases the DNA particles (100 µl) were washed with 400 µl of nuclease-free distilled water and centrifuged for 10 min at 10,000 rpm at room temperature. The supernatant was removed and the DNA particle pellet was re-suspended in 400 µl of nuclease-free distilled water. This was followed by two additional washes after which the DNA particle pellet was re-suspended in a final volume of 50 µL nuclease-free distilled water. The purified DNA particles were then stained with 10×SYBR Green I dye, loaded onto a hemocytometer, imaged under fluorescence microscope.

Purified DNA nanoparticles were stored at 4° C. Note, that DNA particles can be also purified using dialysis or other means.

Coupled In Vitro Transcription and Translation.

eGFP protein expression was performed using an IVTT system purchased from NEB (PURExpress® In Vitro Protein Synthesis Kit). Two separate aliquots containing either native pET29-eGFP plasmid or purified DNA particles were mixed with the IVTT solution and encapsulated in 5 pL droplets using the microfluidics device. The encapsulation process was carried out at 4° C. and protein synthesis performed by incubating the emulsion at 37° C. for ~3 hours. The fluorescence was recorded using an excitation wavelength of 482±12 nm and an emission wavelength of 511±12 nm.

In another example, β-galactosidase enzyme expression was performed using an IVTT system purchased from NEB (PURExpress® In Vitro Protein Synthesis Kit) in the presence of RNase inhibitor Ribolock (Thermo Fisher Scientifc).

IVTT Reaction in 384-Well Format.

The in vitro expression of lacZ in a 384-well format (10 µl/well) was performed by preparing two sets of IVTT reaction mixtures. The first set of reactions was supplemented with 500 to 0.5 ng of pIVEX2.2EM-Lacz-his plasmid, which translated into $10^{11}$-$10^8$ copies of free DNA molecules per 10 µl. The second set of reactions contained purified DNA particles diluted down to 46000, 23000 and 5000 particles per well. Reactions were then incubated at 37° C. for 3 hours to allow gene expression to occur. The catalytic activity of in vitro synthesized lacZ enzyme was recorded by mixing 1 µl of IVTT mix with 9 µL of 1×phi29 buffer (NEB) supplemented with 1 µM fluorescein-di-β-D-galactopyranoside (FDG). The fluorescence signal was measured in a 384-well microtiter plate (polypropylene, black, flat, clear-bottom, Corning) using a Synergy H4 plate reader set at 488 □ 20 nm excitation and 530 □ 20 nm emission wavelengths (gain 75 and 50).

IVTT Reaction in Droplets.

Purified DNA particles stained with ethidium bromide (15 µg/mL) were mixed with the IVTT solution containing 1 µM of β-galactosidase substrate FDG and encapsulated in 18 pl droplets using the 20 µm microfluidics device depicted in FIG. 2B. The flow rates for IVTT reaction encapsulation were 100 µl/h for aqueous phase and 250 µl/h for the carrier oil. The encapsulation time typically took ~20 min, at 4° C. Protein synthesis in vitro was evaluated after incubating the emulsion at 37 □C. for 1 hour. The fluorescence was recorded using fluorescence microscope.

Estimate of the DNA Copy Number in a DNA Particle.

We first recorded images of droplets using 1.5 megapixel digital camera (Ds-Qi1, Nikon, 16 bits). The area of each droplet was composed of 592±32 pixels, whereas the fluorescent spots corresponding to DNA particles comprised 19.4±14.2 pixels. The total amount of DNA in a given droplet (or particle) is proportional to the total fluorescence of that area, which can be expressed as a sum of pixel intensities. Droplets in which DNA was amplified in the presence of pyrophosphatase contained ~$10^5$ copies of amplified DNA as estimated by calibration curve (see Figure S2). The mean pixel intensity of these droplets (n=1174) was equal to 1392±800, which corresponds to 238±137 DNA molecules per pixel. In contrast, pixels inside the droplets in which DNA was amplified in the absence of pyrophosphatase formed clearly distinguishable foreground (fluorescent spots) and background areas. The mean pixel intensity value of fluorescent spots (n=540) was 1775±560, which translates into 304±95 DNA copies per pixel. Multiplying obtained value to the total number of pixels in the foreground leads to the 5970±4320 DNA copies in a single DNA particle. The background pixels outside the fluorescent spot had a mean intensity value of 552±94, which translates into 98±16 DNA molecules per pixel or 54100±8900 copies of free DNA in entire volume of a droplet.

Results

Single DNA Molecule Encapsulation and Amplification.

We first encapsulated pUC19 plasmid DNA in monodisperse 3 pL droplets together with phi29 DNA polymerase, exo-resistant random DNA primers, pyrophosphatase and other reaction components (see Materials and Methods) necessary for DNA synthesis by an MDA mechanism.[9] The plasmid concentration was adjusted so that one droplet contained one DNA molecule on average ($\lambda$=1.0). The microfluidics device used for encapsulation (FIG. 1) was operated at a frequency of 4.6 kHz, allowing collection of $10^6$ droplets in less than an hour.[14] The collected emulsion was incubated at 30° C. for 15 hours to allow the isothermal DNA amplification reaction to occur and then stained with SYBR Green I dye, which becomes fluorescent upon binding dsDNA (FIG. 1).

Figure 2:
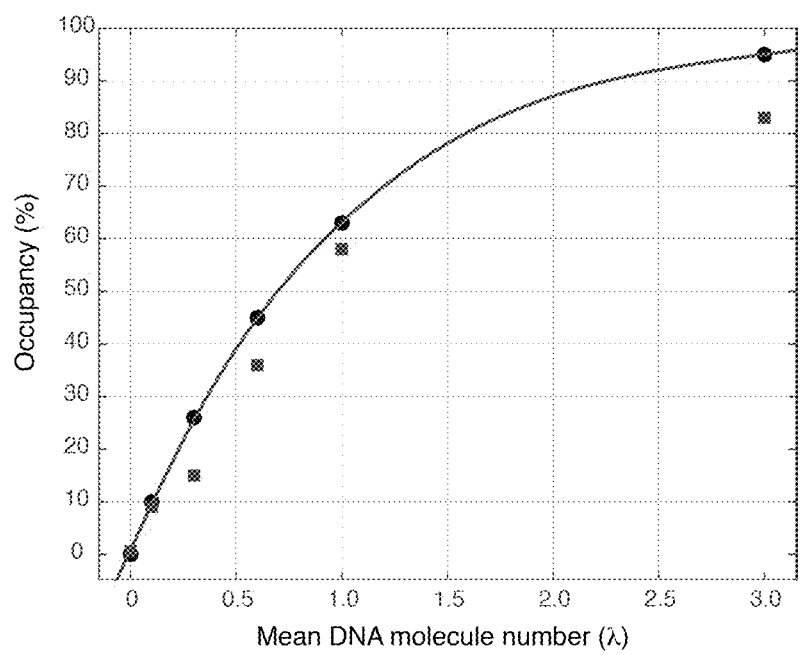
FIG. 2: Occupancy as a function of the mean DNA molecule number per one droplet. Assuming a Poisson distribution, it is possible to calculate the expected percentage of fluorescent droplets (droplets containing DNA) based on the initial DNA concentration in the sample (mean DNA molecule number per one droplet). The theoretically expected number of occupied (DNA containing) droplets is given by the formula.

The Poisson equation predicts that random partitioning of 0.57 pM DNA template into 3 pL droplets ($\lambda$=1.0) will afford a population of 37% empty and 63% occupied droplets, with ~37% of the droplets containing one DNA molecule and ~26% two or more. Digital fluorescence analysis of the emulsion layered on a hemocytometer revealed that ~58% of the droplets were fluorescent after isothermal amplification. Additionally, serial dilutions of the DNA sample confirmed that droplet occupancy followed a Poisson distribution (FIG. 2). The small differences in occupancy between the experimental results and theoretical expectations can be attributed to abortive amplification of damaged DNA plasmids, losses due to nonspecific adsorption in the system, or pipetting errors. As expected, negative controls having no DNA template afforded few fluorescent droplets (~0.4%), corresponding to ~2.0 fM ambient DNA.

Fluorescence imaging of an emulsion after the MDA reaction revealed a mean fluorescence intensity of 440±88 RFU for occupied droplets, which translates to 110±30 ng/µL of DNA or a ~$10^5$-fold amplification of the starting template. Previous reports found a similar degree of amplification when phi29 reactions were performed in bulk[9] or in droplets.[14]

Single DNA Molecule(s) Conversion to the DNA Nanoparticle.

During the course of DNA amplification, we discovered that excluding pyrophosphatase enzyme (PPase) from the reaction mix leads to formation of highly fluorescent nanoparticles inside the droplets (FIG. 3). PPase is an enzyme that catalyzes the hydrolysis of inorganic pyrophosphate into two orthophosphate molecules[21] and is used to increase the amplification yields of nucleic acids.[9] We postulated that during the course of single DNA molecule amplification the condensation of DNA into macromolecular structures can be induced by negatively charged molecules (such as inorganic pyrophosphate) in the presence of counterions (such as magnesium ions, calcium, etc.). To confirm that inorganic pyrophosphate is indeed a prerequisite for formation of condensed DNA nanoparticles we encapsulated 0.23 µM pUC19 DNA ($\lambda$=4·$10^5$) dissolved in 8 mM Tris-HCl buffer [pH 7.6] containing 4 mM sodium pyrophosphate and 10 mM $MgCl_2$, while excluding other components such as the phi29 enzyme, primers, and dNTPs from the reaction mix. As expected, we observed formation of fluorescent precipitants in the droplets (FIG. 4), confirming that inorganic pyrophosphate and magnesium ions are major triggers for the formation of DNA nanoparticles. In agreement with our observations, others have recently reported the formation of DNA/RNA:pyrophosphate:magnesium complexes under PCR/RCA conditions.[17, 22, 23] Taken together, our findings and literature reports allow us to conclude that inorganic pyrophosphate, produced during the isothermal DNA amplification reaction [10], associates with magnesium ions and promotes condensation of newly synthesized DNA in the particle.

Figure 7:
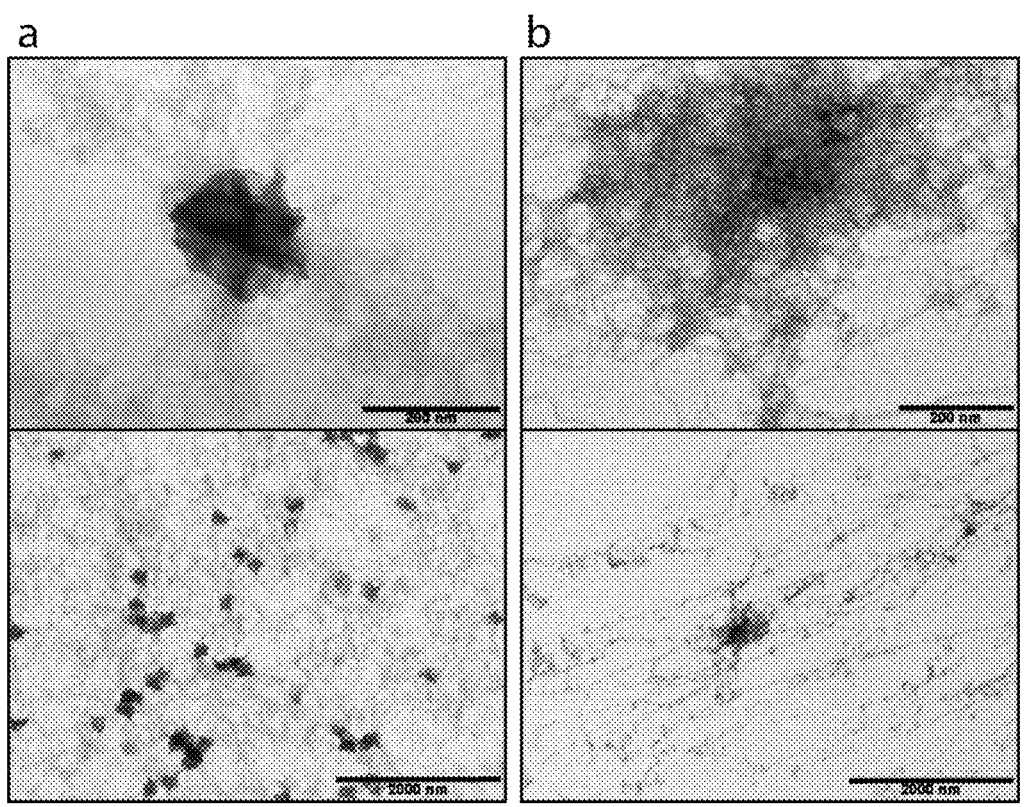

Electrophoretic analysis confirmed that DNA amplification, with or without PPase, was specific (FIG. 5). We used digital image analysis to quantify the number of DNA copies and found that single DNA nanoparticles contained ~6,000 copies of the original template (Material and Methods). To gain further insight into structural features of the DNA material produced during isothermal amplification, we disrupted the droplets and analyzed the released material by transmission electron microscopy (TEM), scanning electron microscopy (SEM), atomic force microscopy (AFM) and dynamic light scattering (DLS). The DLS measurements confirmed the presence of particles with a diameter of 152±37 nm (FIG. 6a), in good agreement with the AFM measurements (FIG. 6b). The TEM and SEM analysis revealed individual, densely packed nanoparticles of uniform size and a petal-like surface structure (FIG. 6c and FIG. 6d). Similar crystalline-like, globular microstructures were recently generated from short, circular DNA [24, 25] and RNA [26] templates. Nevertheless, despite detailed microscopic characterization of these DNA/RNA microstructures, the importance of pyrophosphate:magnesium complexes for the nucleation and condensation process remained unappreciated. Performing the MDA reaction in bulk at different template concentrations (0.1-100 pM) led to formation of DNA macromolecules, albeit without clearly defined structure (FIG. 7).

Proving Biological Functionality of DNA Nanoparticle.

A variety of biological and biochemical applications would benefit from clonally amplified DNA that could serve as a template for in vitro protein assays. For example, in vitro protein expression offers major advantages for screening of new enzymatic activities since it does not rely on a living host to produce the target protein. To test whether individual DNA nanoparticles (DNA-NPs) could serve as templates for gene expression, we performed IVTT reactions (FIG. 8). To monitor protein production, we used a pET29b(+) vector encoding enhanced green fluorescent protein (eGFP) under the control of the T7 promoter. DNA-NPs were first prepared from this plasmid encapsulated in droplets and then purified by preparative agarose gel electrophoresis and centrifugation. The purified material largely retained its densely packed structure, judging from TEM images of purified particles (FIG. 9). Additionally, electrophoretic analysis of the sample confirmed highly specific amplification of the original template (FIG. 10).

To evaluate the in vitro biological functionality of the synthesized material we added purified DNA-NPs to the IVTT mix and created 5 pL droplets using the same microfluidics device shown in FIG. 1. We used diluted suspensions of DNA-NPs (λ=0.05) to ensure that each droplet carries no more than one DNA nanoparticle. The collected emulsion was incubated at 37° C. for 3 hours to allow in vitro gene expression to occur. Fluorescence analysis confirmed that droplets containing a single DNA-NP expressed high levels of eGFP protein, as evidenced by the appearance of highly fluorescent droplets (FIG. 8b). As expected, further dilution of the purified DNA nanoparticles reduced the number of fluorescent droplets generated by the IVTT reaction, but the expression levels of eGFP in individual droplets remained high (FIG. 11). Considering that a single DNA-NP carries approximately 6000 copies of an initial template (Supplementary Note 1) we compared eGFP yields for droplets containing similar amount (7,000 copies) of free plasmid to droplets containing a single DNA-NP and found that the latter gave ~2.5-times higher eGFP expression (FIG. 10). Although the protein levels produced from a single DNA nanoparticle as a template were broadly distributed (coefficient of variation, CV=0.33), more importantly the overall yield of in vitro expressed protein was much higher than could be obtained from a single DNA plasmid molecule (FIG. 10). Traces of free DNA molecules that co-purified with the DNA-NPs showed negligible levels of eGFP expression (background droplets in the right panel of FIG. 10b). These results indicate that a DNA nanoparticle produced from a single-copy template contains a sufficiently large number of functional gene copies to afford high yields of protein.

To further validate in vitro protein synthesis yields we used a bulk format. We added ~$10^4$ and ~$10^3$ purified DNA nanoparticles (where a single particle has ~$6 \cdot 10^3$ clonal copies of the eGFP gene) to 10 μL IVTT mix and followed protein expression levels by monitoring green fluorescence over time. As a control, we prepared 10 μL IVTT samples containing between $10^5$ and $10^9$ copies of the native pET29-eGFP plasmid per sample. The results shown in FIG. 12 confirmed that protein yields were considerably higher for the sample containing DNA nanoparticles. Even when the number of gene copies encoded by a free plasmid DNA was comparable to the number of gene copies encoded by DNA nanoparticles, the yields of in vitro synthesized protein were significantly higher for samples containing DNA nanoparticles (FIG. 12). The high local concentration of gene copies in a single DNA nanoparticle is most likely responsible for the improved expression levels. Other factors may also contribute synergistically. For example, high local concentrations of DNA will prevent T7 RNA polymerase from diffusing away; after transcription of the first template, the enzyme will more likely bind a nearby promoter as opposed to diffusing into the bulk. Condensed DNA structures, in the form of hydrogels, have similarly been shown to increase RNA and protein yields in vitro. [15] Taking advantage of the densely packed DNA structure, conventional DNA purification techniques can be used to separate DNA-NPs from the original reaction components (salts, enzymes). Such an option will be important for performing sequential multi-step reactions [27, 28] that are inhibited or incompatible with standard biochemical conditions.

As exemplified in previous work [14], the DNA amplification mix may inhibit the subsequent protein synthesis step due to differences in salt concentration, pH and other components. Nonetheless, purified DNA-NPs not only retain their compact structure but also, by virtue of the large number of clonal gene copies, increase the yield of protein produced in vitro. The importance of in vitro protein synthesis is easy to appreciate in the context of directed evolution, proteomics, synthetic biology or various types of screening assays that rely on cell-free systems.

To further prove the applicability of DNA particles for biochemical assays we first emulsified 3.6 kb circular nucleic acid molecules and multiple displacement amplification (MDA) reagents into 3 pl droplets using 10 μm deep microfluidics device (FIG. 1). The MDA reaction mix contained DNA template (pIVEX2.1-lacZ-his plasmid encoding enzyme β-galactosidase), phi29 DNA polymerase, exo-resistant oligonucleotides and other reagents needed for efficient isothermal DNA amplification reaction (see Material and Methods). We used diluted DNA concentrations (0.63 pM) so that one droplet would contain 1 molecule on average ($\lambda\sim 1.0$). Droplets loaded with MDA reaction mix were collected off-chip into a collection tube, and incubated for 16 hours at 30° C. to initiate the isothermal DNA amplification reaction by phi29 DNA polymerase. After off-chip incubation droplets were stained with SYBR Green I dye, which passively migrates between the droplets and becomes fluorescent upon binding dsDNA. In agreement with the example presented above the amplified DNA formed condensed particles clearly visible under the fluorescent microscope (FIG. 13).

The transmission electron microscopy (TEM) and scanning electron microscopy (SEM) analysis revealed densely packed globular shape particles having the average size of 1233±266 nm (FIG. 14). Since the amount of amplified DNA during MDA reaction increases geometrically over time [9], it would be reasonable to assume that longer incubations should increase the size of DNA particles. However, extended incubations have not affected DNA nanoparticle's size, suggesting that MDA reaction in 3 pl volume droplets has been largely completed in 16 hours window (FIG. 15). Similar studies have shown that the yield of amplified DNA in droplets is limited by the available dNTPs and primers [29]. In addition, it appears that 65° C. heat-inactivation step, which terminates the MDA reaction by denaturating phi29 DNA polymerase, causes DNA particles to break into smaller pieces as witnessed by appearance of two particle subpopulations (data not shown). We further investigated the external features of the DNA particles by TEM, and compared them to the inorganic Mg-PP$_i$ particles lacking DNA template. To produce inorganic Mg-PP$_i$ particles we mixed 10 mM MgCl$_2$ and 5 mM sodium pyrophosphate (Na$_4$P$_2$O$_7$) in deionized water, heated reaction mix for 5 min at 70° C. and after cooling down to room temperature (21° C.) immediately imaged sample under TEM. The TEM analysis revealed spiky crystalline spherulites of approximately ~200 nm size (FIG. 15) similar to calcium orthophosphate cements [30]. When the same Mg-PP$_i$ particles were mixed with 56 nM of plasmid DNA (~300 ng/µl) the spikiness features turned into the petal-like structures closely resembling those DNA nanoparticles produced during the MDA reaction (see FIG. 15). These results suggest that inorganic Mg-PP$_i$ particles adsorb free DNA molecules into condensed macromolecular structures and therefore may act as a nucleation seed during the MDA reaction. In support of this notion, Shopsowitz et al., showed that RNA:Mg:PP$_i$ particles produced during rolling circle transcription can be stripped off the RNA to retain inorganic Mg$_2$P$_2$O$_7$·3.5H$_2$O scaffold [17]. Others have also shown the generation of various macromolecular nucleic acid structures that are likely to be mediated through multiple ion bridges coordinated by magnesium ions and pyrophosphate [24, 31-34]. Given our results and previous reports it is appealing to think that under certain environmental conditions the inorganic pyrophosphate and divalent ions (magnesium, calcium, etc.) complexes may also induce genomic DNA condensation in cells. Interestingly, earlier research has described bacterial chromosomal DNA condensation (crystallization) induced by negatively charged Dps proteins and divalent cations [35, 36]; in this context the inorganic pyrophosphate in principle could mimic the function of the Dps protein.

To verify whether clonally amplified DNA template condensed into DNA:Mg:PP$_i$ particles support the in vitro transcription-translation reaction we have amplified DNA carrying lacZ gene by performing MDA reaction in droplets as described above. After the MDA reaction, DNA particles were released from droplets and purified by brief digestion with restriction endonuclease followed by centrifugation (see Materials and Methods section). TEM analysis showed that DNA particles retained their condensed structure during purification process (FIG. 16). The purified DNA:Mg:PP$_i$ particles were then added to the IVTT reaction mixture in a 384-well plate and incubated for 3 hours to allow lacZ protein synthesis to occur. As a control, we performed IVTT reactions having varying amounts of pIVEX-lacZ-his plasmid ranging from $10^{11}$ to $10^8$ template copies in a 10 µl reaction volume. The enzymatic activity of the synthesized protein was then evaluated using a fluorogenic assay, which is based on hydrolysis of FDG (fluorescein-di-β-D-galactopyranoside) substrate to produce fluorescent product (fluorescein). Results presented in FIG. 17 suggest that DNA particles can serve as template for protein synthesis in vitro, in agreement with previous work [37]. The yield of in vitro synthesized protein from only ~$10^4$-$10^3$ DNA particles was approximately equal to the amount of protein produced from ~$10^8$-$10^9$ copies of free DNA plasmid, thus suggesting that after purification single DNA particle retains ~$10^6$-$10^5$ copies of a functional gene. Alternatively, it could be that condensed DNA structures enhance the transcription-translation reaction, similarly to the DNA microgels reported previously [15]. To further validate the feasibility of DNA particles use as a biomaterial for the droplet-based assays we co-encapsulated purified DNA:Mg:PP$_i$ particles, IVTT reaction mix and FDG substrate in 18 pl droplets using 20 µm deep microfluidics device depicted in FIG. 13. The collected IVT droplets were incubated at 37° C. for 1 hour to allow lacZ gene expression to occur and imaged under fluorescent microscope. We used DNA particle dilution at $\lambda\sim 0.1$ to reduce the chance of having two particles in a droplet: in these conditions ~89% droplets would contain 0 particles, 10% would contain 1 DNA particle and ~0.5% of all droplets would contain ≥2 DNA particles. As expected, the microscopic analysis revealed droplet subpopulation (~10%) with bright fluorescent signal, thus indicating the reaction product formation due to catalytic activity of β-galactosidase. The fluorescence signal corresponding to the enzymatic activity varied among droplets (coefficient of variation ~20%) and could be attributed to the differences of purified particle size (FIG. 16), or varying amounts of DNA template incorporated in a particle. Nonetheless, considering early microfluidic systems [14] in which droplet reinjection and fusion steps were needed to perform protein synthesis from the amplified DNA template, this work significantly simplifies the use of in vitro expression assays and therefore could open new possibilities for directed evolution and synthetic biology fields. Finally, the better understanding of a mechanism by which amplified DNA is incorporated into macromolecular DNA:Mg:PP$_i$ structured during DNA amplification may facilitate the improvement of whole genome amplification [38] and other isothermal nucleic acid amplification techniques [10].

To show that DNA particles can be also generated in different reaction format (e.g. droplets, tubes, wells, chambers) we mixed DNA plasmid pUC19 with MDA reagents (pUC19 DNA plasmid ~0.001 ng/uL, random hexamer primers 10 µM, Pluronic F127 0.4% (w/v), dNTPs 1 mM, 1×phi29 polymerase buffer and phi29 DNA polymerase 0.8 U/uL) and incubated reaction mix for 16 hours at 30° C. After incubation, reaction product was imaged under transmission electron microscope (TEM) revealing the appearance of individual, dense, crystalline-like particles surrounded by the mesh (FIG. 18). These results provide evidence that single-DNA molecules can be converted into DNA particles using different reaction formats such as performing DNA amplification reaction in tube(s), well(s), chamber(s), etc. Therefore, DNA particle synthesis can be performed using different systems and/or reaction conditions.

1. Ottesen, E. A., et al., *Microfluidic digital PCR enables multigene analysis of individual environmental bacteria.* Science, 2006. 314(5804): p. 1464-7.
2. Beer, N. R., et al., *On-chip, real-time, single-copy polymerase chain reaction in picoliter droplets.* Anal Chem, 2007. 79(22): p. 8471-5.
3. Vogelstein, B. and K. W. Kinzler, *Digital PCR.* Proc Natl Acad Sci USA, 1999. 96(16): p. 9236-41.
4. Heyries, K. A., et al., *Megapixel digital PCR.* Nature Methods, 2011. 8(8): p. 649-U64.
5. Devonshire, A. S., et al., *Highly Reproducible Absolute Quantification of Mycobacterium tuberculosis Complex by Digital PCR.* Anal Chem, 2015. 87(7): p. 3706-3713.
6. Day, E., P. H. Dear, and F. McCaughan, *Digital PCR strategies in the development and analysis of molecular biomarkers for personalized medicine.* Methods, 2013. 59(1): p. 101-107.
7. Pekin, D., et al., *Quantitative and sensitive detection of rare mutations using droplet-based microfluidics.* Lab on a Chip, 2011. 11(13): p. 2156-2166.
8. Bizouarn, F., *Introduction to Digital PCR.* Quantitative Real-Time Pcr: Methods and Protocols, 2014. 1160: p. 27-41.
9. Dean, F. B., et al., *Rapid amplification of plasmid and phage DNA using Phi 29 DNA polymerase and multiply-primed rolling circle amplification.* Genome Res, 2001. 11(6): p. 1095-9.
10. Zhao, Y., et al., *Isothermal Amplification of Nucleic Acids.* Chem Rev, 2015. 115(22): p. 12491-545.
11. Shimizu, Y., et al., *Cell-free translation reconstituted with purified components.* Nat Biotechnol, 2001. 19(8): p. 751-5.
12. Asahara, H. and S. Chong, *In vitro genetic reconstruction of bacterial transcription initiation by coupled synthesis and detection of RNA polymerase holoenzyme.* Nucleic Acids Res, 2010. 38(13): p. e141.
13. Lesley, S. A., M. A. Brow, and R. R. Burgess, *Use of in vitro protein synthesis from polymerase chain reaction-generated templates to study interaction of Escherichia coli transcription factors with core RNA polymerase and for epitope mapping of monoclonal antibodies.* J Biol Chem, 1991. 266(4): p. 2632-8.
14. Mazutis, L., et al., *Droplet-based microfluidic systems for high-throughput single DNA molecule isothermal amplification and analysis.* Anal Chem, 2009. 81(12): p. 4813-21.
15. Park, N., et al., *A cell-free protein-producing gel.* Nat Mater, 2009. 8(5): p. 432-7.
16. Oetting, F. L. and R. A. McDonald, *THE THERMODYNAMIC PROPERTIES OF MAGNESIUM ORTHOPHOSPHATE AND MAGNESIUM PYROPHOSPHATE.* The Journal of Physical Chemistry, 1963. 67(12): p. 2737-2743.
17. Shopsowitz, K. E., et al., *RNAi-microsponges form through self-assembly of the organic and inorganic products of transcription.* Small, 2014. 10(8): p. 1623-33.
18. Bloomfield, V. A., *DNA condensation by multivalent cations.* Biopolymers, 1997. 44(3): p. 269-282.
19. Bloemberg, G. V., et al., *Simultaneous imaging of Pseudomonas fluorescens WCS365 populations expressing three different autofluorescent proteins in the rhizosphere: new perspectives for studying microbial communities.* Mol Plant Microbe Interact, 2000. 13(11): p. 1170-6.
20. Mazutis, L., et al., *Single-cell analysis and sorting using droplet-based microfluidics.* Nat Protoc, 2013. 8(5): p. 870-91.
21. Sperow, J. W., et al., *Yeast inorganic pyrophosphatase. VI. Studies on specificity and mechanism.* J Biol Chem, 1973. 248(6): p. 2062-5.
22. Danilevich, V. N., et al., *The structural peculiarities of condensed DNA micro-and nanoparticles formed in PCR.* Journal of Biomolecular Structure & Dynamics, 2014. 32(12): p. 1979-1992.
23. Danilevich, V. N., et al., *New insight into formation of DNA-containing microparticles during PCR: the scaffolding role of magnesium pyrophosphate crystals.* Journal of Biomolecular Structure and Dynamics, 2015: p. 1-15.
24. Zhu, G. Z., et al., *Noncanonical Self-Assembly of Multifunctional DNA Nanoflowers for Biomedical Applications.* Journal of the American Chemical Society, 2013. 135(44): p. 16438-16445.
25. Hu, R., et al., *DNA Nanoflowers for Multiplexed Cellular Imaging and Traceable Targeted Drug Delivery.* Angewandte Chemie-International Edition, 2014. 53(23): p. 5821-5826.
26. Lee, J. B., et al., *Self-assembled RNA interference microsponges for efficient siRNA delivery.* Nature Materials, 2012. 11(4): p. 316-322.
27. Mazutis, L., et al., *Multi-step microfluidic droplet processing: kinetic analysis of an in vitro translated enzyme.* Lab on a Chip, 2009. 9(20): p. 2902-8.
28. Ryckelynck, M., et al., *Using droplet-based microfluidics to improve the catalytic properties of RNA under multiple-turnover conditions.* RNA, 2015. 21(3): p. 458-469.
29. Mazutis, L., et al., *Droplet-based microfluidic systems for high-throughput single DNA molecule isothermal amplification and analysis.* Analytical Chemistry, 2009. 81(12): p. 4813-21.
30. Dorozhkin, S. V., *Self-setting calcium orthophosphate formulations.* J Funct Biomater, 2013. 4(4): p. 209-311.
31. Yata, T., et al., *Efficient amplification of self-gelling polypod-like structured DNA by rolling circle amplification and enzymatic digestion.* Sci Rep, 2015. 5: p. 14979.
32. Roh, Y. H., et al., *A Multi-RNAi Microsponge Platform for Simultaneous Controlled Delivery of Multiple Small Interfering RNAs.* Angew Chem Int Ed Engl, 2016. 55(10): p. 3347-51.
33. Lee, S. Y., et al., *Biophysical and chemical handles to control the size of DNA nanoparticles produced by rolling circle amplification.* Biomaterials Science, 2016. 4(9): p. 1314-1317.
34. Kahn, J. S., et al., *DNA Microgels as a Platform for Cell-Free Protein Expression and Display.* Biomacromolecules, 2016. 17(6): p. 2019-2026.
35. Frenkiel-Krispin, D., et al., *Regulated phase transitions of bacterial chromatin: a non-enzymatic pathway for generic DNA protection.* EMBO J, 2001. 20(5): p. 1184-91.
36. Wolf, S. G., et al., *DNA protection by stress-induced biocrystallization.* Nature, 1999. 400(6739): p. 83-85.
37. Galinis, R., et al., *DNA Nanoparticles for Improved Protein Synthesis In Vitro.* Angew Chem Int Ed Engl, 2016. 55(9): p. 3120-3.
38. Sidore, A. M., et al., *Enhanced sequencing coverage with digital droplet multiple displacement amplification.* Nucleic Acids Res, 2016. 44(7): p. e66.

The invention claimed is:

1. A method of generating individual particles each using a single nucleic acid molecule template by means of enzymatic amplification in aqueous micro-droplets, wherein each particle comprises nucleic acid(s), pyrophosphate(s), and metal ions, wherein said method of producing the individual particles comprises:
   (i) providing one or more nucleic acid molecule templates to be amplified;
   (ii) providing nucleic acid amplification reaction ingredients including polymerase, primers, dNTP, salts, non-ionic detergent(s);
   (iii) partitioning nucleic acid molecules and amplification reaction ingredients in the aqueous micro-droplets using a microfluidics system such that one aqueous micro-droplet contains, on average, no more than one nucleic acid molecule template;
   (iv) incubating for a given period of time to allow nucleic acid amplification and formation of the particles to occur; and
   (v) releasing particles from the aqueous micro-droplets.

2. The method of claim 1, wherein the nucleic acid molecule template is DNA, RNA, or a modified nucleic acid.

3. The method of claim 1, wherein at least one nucleic acid molecule in each particle has a nucleotide sequence of one of the nucleic acid molecule templates.

4. The method of claim 1, wherein the step of forming a particle further comprises amplifying the nucleic acid molecule template using DNA polymerase or RNA polymerase.

5. The method according to claim 4, wherein a plurality of micro-channels of a fluid merge into a single micro-channel, and wherein a depth of the micro-channels is in a range from 1 μm to 1000 μm.

6. The method of claim 1, wherein the nucleic acid molecule(s) within a particle comprise single-stranded, double-stranded, triple-stranded nucleic acids or a combination thereof.

7. The method of claim 1, wherein the size of a single particle is greater than 10 nm, 100 nm, 1000 nm or 10 μm.

8. The method of claim 1, wherein said particles are purified from the reaction mixture.

9. The method according to claim 1, wherein the microfluidics system comprises:
   (i) at least two inlets;
   (ii) at least two microfluidic channels;
   (iii) a flow focusing junction;
   (iv) droplet collection outlet; and
   (v) at least one of the at least two microfluidics channels connect the flow focusing junction with the outlet.

10. The method of claim 1, wherein the formation of the particle(s) occurs in aqueous droplets no larger than 1 microliter volume and no smaller than 1 femtoliter volume.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Forward primer

<400> SEQUENCE: 1
taataacata tggtgagcaa gggcg                                               25

<210> SEQ ID NO 2
<211> LENGTH: 25
<212> TYPE: DNA
<213> ORGANISM: Artificial Sequence
<220> FEATURE:
<223> OTHER INFORMATION: Reverse primer

<400> SEQUENCE: 2
ttattactcg agcttgtaca gctcg                                               25
```